US007696364B2

(12) United States Patent
Bonrath et al.

(10) Patent No.: US 7,696,364 B2
(45) Date of Patent: Apr. 13, 2010

(54) PROCESS FOR THE MANUFACTURE OF ALKENYLATED HYDROXYLATED AROMATIC COMPOUNDS, OF CHROMAN COMPOUNDS AND OF THEIR ACYLATED DERIVATIVES

(75) Inventors: Werner Bonrath, Freiburg (DE); Yann Foricher, Riedisheim (FR); Thomas Netscher, Bad Krozingen (DE); Angela Wildermann, Bad Säckingen (DE)

(73) Assignee: DSM IP Assets B.V. a Netherlands Corporation, Heerlen (NL)

( * ) Notice: Subject to any disclaimer, the term of this patent is extended or adjusted under 35 U.S.C. 154(b) by 1169 days.

(21) Appl. No.: 11/005,402

(22) Filed: Dec. 6, 2004

(65) Prior Publication Data

US 2005/0171362 A1 Aug. 4, 2005

(51) Int. Cl.
*C07D 311/11* (2006.01)
*B01J 27/06* (2006.01)
*B01J 27/138* (2006.01)

(52) U.S. Cl. .................. 549/411; 502/224; 502/226; 502/227

(58) Field of Classification Search .................. 549/411; 502/224, 226, 227
See application file for complete search history.

(56) References Cited

U.S. PATENT DOCUMENTS

| | | | |
|---|---|---|---|
| 3,980,797 A * | 9/1976 | Jonas et al. | 514/220 |
| 6,180,557 B1 | 1/2001 | Choudhary et al. | |
| 6,420,301 B1 * | 7/2002 | Kristen et al. | 502/155 |
| 6,459,000 B1 | 10/2002 | Choudhary et al. | |
| 6,909,020 B2 * | 6/2005 | Edwards et al. | 568/671 |
| 2005/0277777 A1 | 12/2005 | Bonrath et al. | |

FOREIGN PATENT DOCUMENTS

| | | |
|---|---|---|
| EP | 0 694 541 A1 | 1/1996 |
| EP | 1 000 940 A1 | 5/2000 |
| JP | 9-241184 | 9/1997 |
| KR | 2000 065376 | 11/2000 |
| WO | WO 03/028883 A1 | 4/2003 |

OTHER PUBLICATIONS

Chauhan et al., "*Indium Thiflate: An Efficient Catalyst For Acylation Reactions*," XP-00233479 & Synlett No. 11, pp. 1743-1744 (1999).
Lim, H.J. et al, "*A New Direct Allylation of the Aromatic Compounds With Allylic Chlorides Catalyzed By Indium Metal*," XP-002333480 & Tetrahedron Letters, No. 40, pp. 1547-1550 (1999).
Chakraborti and Gulhane, "*Indium(II) chloride as a new, highly efficient, and versatile catalyst for acylation of phenols, thiols, alcohols, and amines*," XP-002333481 & Tetrahedron Letters, No. 44, pp. 6749-6753 (2003).
Derwent Database English language Abstract No. XP-002333485 & JP 09 241184.
Caplus Online! Database English language Abstract No. XP-002333482 & KR 2000 065376.
Caplus Online! Database English language Abstract No. XP-002333483 & Database accession No. 2002:775758.
Caplus Online! Database English language Abstract No. XP-002333484 & Database accession No. 2000:796615.
Ranu, B.C., "*Indium Metal and Its Halides in Organic Synthesis*." Eur. J. Org. Chem., pp. 2347-2356 (2000).
Ullman's Encylcopedia of Industrial Chemistry, vol. A27, 5$^{th}$ Edition, pp. 484-485 (1996).

* cited by examiner

Primary Examiner—Janet L. Andres
Assistant Examiner—Raymond Covington
(74) Attorney, Agent, or Firm—Hoxie & Associates LLC

(57) ABSTRACT

The present invention relates to a process for the manufacture of alkenylated aromatic compounds featuring at least one hydroxy group, their ring-closure reactions to 5 chroman derivatives, as well as the acylation of the latter and the aromatic compounds featuring at least one hydroxy group themselves. The present invention relates especially to a process for the manufacture of tocol, tocopherols and their alkanoates such as (x-tocopherol (TCP) and alkanoates (TCPA) thereof, preferably (x-toeopheryl acetate (TCPAc). The processes of the present invention are characterized in that at least one step of the processes is carried out in the presence of an indium salt as the catalyst.

30 Claims, No Drawings

PROCESS FOR THE MANUFACTURE OF ALKENYLATED HYDROXYLATED AROMATIC COMPOUNDS, OF CHROMAN COMPOUNDS AND OF THEIR ACYLATED DERIVATIVES

The present invention relates to a novel process for the manufacture of alkenylated aromatic compounds featuring at least one hydroxy group, their ring-closure reactions to chroman derivatives, as well as the acylation of the latter and the aromatic compounds featuring at least one hydroxy group themselves. The present invention relates especially to a process for the manufacture of tocols, tocopherols and their alkanoates such as α-tocopherol (TCP) and alkanoates (TCPA) thereof, preferably α-tocopheryl acetate (TCPAc). The processes of the present invention are characterized in that at least one step of the processes is carried out in the presence of an indium salt as the catalyst.

As starting materials for the manufacture of TCP and TCPA either a mixture of 2,3,5-trimethylhydroquinone (TMHQ) or a 2,3,6-trimethylhydroquinone-1-alkanoate and a compound selected from the group consisting of phytol (PH), isophytol (IP) and (iso)phytol derivatives, or the "open ring" compound 2-phytyl-3,5,6-trimethyl-hydroquinone (PTMHQ), a 3-phytyl-2,5,6-trimethylhydroquinone-1-alkanoate (PTMHQA) or an isomer thereof are used.

Thus, an object of the present invention is the use of an indium salt as the catalyst in Friedel-Crafts alkylation reactions of aromatic compounds featuring at least one hydroxy group and ring-closure reactions of resulting "open ring" products to produce chroman-ring compounds in organic solvents. According to another aspect of the invention indium salts can be used as the catalyst in processes for the manufacture of tocyl alkanoates, tocopheryl alkanoates and alkanoates of aromatic compounds featuring at least one hydroxy group by reacting tocol, tocopherols and aromatic compounds featuring at least one hydroxy group, respectively, with an acylating agent.

As is known, (all-rac)-α-tocopherol (or as it has mostly been denoted in the prior art, "d,l-α-tocopherol") is a mixture of four diastereomeric pairs of enantiomers of 2,5,7,8-tetramethyl-2-(4',8',12'-trimethyl-tridecyl)-6-chromanol (α-tocopherol), which is the biologically most active and industrially most important member of the vitamin E group.

Many processes for the manufacture of "d,l-α-tocopherol" (referred to as such in the literature reviewed hereinafter) and its acetate by the reaction of TMHQ/2,3,6-trimethyl-hydroquinone-1-acetate (TMHQAc) with IP or PH in the presence of a catalyst or a catalyst system and in a solvent or solvent system are described in the prior art.

One example therefor is EP-A 0 694 541 which describes the reaction of TMHQ and IP, PH or a PH derivative in the presence of a mineral acid, a Lewis acid, an acidic ion exchange resin or a triflate, nitrate or sulfate of Sc, Y or a lanthanide element as the catalyst.

Another example is EP-A 1 000 940, where bis-(trifluoromethylsulphonyl)imide [$HN(SO_2CF_3)_2$] or a metal salt thereof of the formula $M(N(SO_2CF_3)_2)_n$ is used as the catalyst, wherein M is a metal atom such as for example boron, magnesium, aluminum, silicon, scandium, titanium, vanadium, manganese, iron, cobalt, nickel, copper, zinc, yttrium, zirconium, rhodium, palladium, silver, tin, lanthanum, cerium, neodymium, praseodymium, europium, dysprosium, ytterbium, hafnium, platinum and gold, and n is the corresponding valency (1, 2, 3 or 4) of the metal atom M, and supercritical $CO_2$ or $N_2O$ is used as the solvent. A cosolvent may also be used, which is a lower aliphatic alkanol, ketone or hydrocarbon.

TCP can be converted into its acetate, succinate and further known application forms by standard methods, e.g. as described in Ullmann's Encyclopedia of Industrial Chemistry, Vol. A27, $5^{th}$ edition, pages 484 to 485, VCH Verlagsgesellschaft mbH, D-69451 Weinheim, 1996. In contrast to TCP which is labile against oxidative conditions, the esters (TCPA) are more stable and more convenient to handle.

Concerning the known use of indium salts in the prior art, the following selected literature is discussed: According to U.S. Pat. No. 6,180,557 B1 supported catalysts of the general formula $A_aMZ_b(c)/S$ are used as the catalysts for Friedel-Crafts reactions such as alkylation, aralkylation, acylation or aroylation of aromatic compounds, wherein A is selected from the chemical elements Ga, Al, B, Zn, Fe, Sn, Ti, Th, Zr or a mixture of two or more thereof; M is selected from the chemical elements In, Tl or a mixture thereof; Z is selected from the chemical elements O, Cl, Br or I; S is a porous catalyst support or carrier; a is the A/M mole ratio in the range of about 0.001 to about 100; b is the number of atoms of Z needed to fulfill the valency requirement of the metallic elements $A_aM$ present in the supported catalyst; and c is the weight percentage loading of $A_aMZ_b$ deposited on said catalyst support or carrier (S) in the range of about 0.5 wt % to about 50 wt %. In example 13 e.g. $Ga_{12.6}InCl_{40.8}$ (11.0 weight-%)/Montmorillonite K10 catalyzes the aralkylation of benzene, anisole, phenol, p-xylene, mesitylene and toluene with benzyl chloride or bromide.

According to WO 03/028883 an "ionic liquid catalyst system" consisting of an ionic liquid and indium(III) halide components is the catalyst in Friedel-Crafts alkylation and acylation reactions.

European Journal of Organic Chemistry 2000, 2347-2356 describes inter alia the use of indium(III) iodide as catalyst for transesterification processes.

The object of the present invention is to provide a process for the manufacture of alkenylated aromatic compounds featuring at least one hydroxy group and of the ring-closed products thereof such as α-tocopherol and its alkanoates in the presence of a catalyst and in a solvent wherein a catalyst is used which catalyzes the desired reaction as selectively as possible and in high yields. Furthermore, the catalyst should display its activity in small, really catalytic, amounts and should be readily separable and re-usable several times.

According to the present invention this object is achieved by the use of indium salts as the catalysts. It has been surprisingly found that indium salts are most suitable catalysts for the condensation reaction of aromatic compounds featuring at least one hydroxy group such as TMHQ or TMHQA with compounds containing a double bond such as IP, PH or a derivative thereof and for the ring closure reaction of alkenylated phenols such as PTMHQ or PTMHQA and/or isomers thereof to produce chroman derivatives such as α-tocopherol as well as for the acylation of aromatic compounds featuring at least one hydroxy group, tocols and tocopherols.

Process for the Alkenylation of Aromatic Compounds Featuring at Least One Hydroxy Group (Friedel-Crafts Alkylation of ArOH)

In one aspect, the present invention is concerned with a process for the alkenylation of an aromatic compound featuring at least one hydroxy group (ArOH) with a compound of the formula III and/or IV in an organic solvent

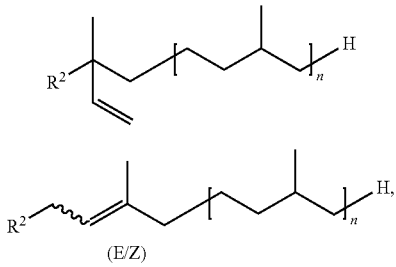

ArOH comprising at least one unsubstituted position as well as 0 to 4 linear $C_{1-6}$-alkyl groups and a total of 1 to 3 hydroxy groups, $R^2$ being hydroxy, acetyloxy, benzoyloxy or halogen, n being an integer from 0 to 3, and the reaction being carried out in the presence of an indium salt as the catalyst. This process is referred to as PROCESS 1 hereinafter.

Concerning the moiety $R^2$ of the compound III and/or IV: preferably $R^2$ is hydroxy, acetyloxy, benzoyloxy, chlorine or bromine, more preferably $R^2$ is hydroxy, acetyloxy or chlorine, most preferably $R^2$ is hydroxy.

Concerning the integer n: Preferably n is 3.

The term "aromatic compounds featuring at least one hydroxy group (ArOH)" comprises phenols which have 0 to 4 linear $C_{1-6}$-alkyl groups and a total of 1 to 3 hydroxy groups as well as at least one unsubstituted position; 1-naphthols, which have 0 to 4 linear $C_{1-6}$-alkyl groups and a total of 1 to 3 hydroxy groups as well as at least one unsubstituted position with the proviso that the unsubstituted position is ortho to a hydroxy group; and 2-naphthols, which have 0 to 4 linear $C_{1-6}$-alkyl groups and a total of 1 to 3 hydroxy groups as well as at least one unsubstituted position with the proviso that the unsubstituted position is ortho to a hydroxy group.

Preferably the phenols, 1-naphthols and 2-naphthols each have 1 to 3 linear $C_{1-6}$-alkyl groups and a total of 1 to 3 hydroxy groups as well as at least one unsubstituted position with the proviso that the or an unsubstituted position is ortho to a hydroxy group. More preferably the phenols, 1-naphthols and 2-naphthols each have 1 to 3 $C_{1-2}$-alkyl groups and a total of 1 to 3 hydroxy groups as well as at least one unsubstituted position with the proviso that the or an unsubstituted position is ortho to a hydroxy group. Most preferably the phenols, 1-naphthols and 2-naphthols each have 1 to 3 methyl groups and a total of 1 to 3 hydroxy groups as well as at least one unsubstituted position with the proviso that the or an unsubstituted position is ortho to a hydroxy group.

From the preferred phenols, 1-naphthols and 2-naphthols cited above especially preferred are phenols with the following formula II

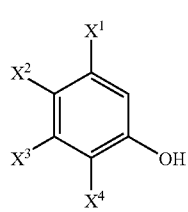

with $X^1$, $X^2$, $X^3$ and $X^4$ being independently from each other hydrogen, hydroxy or linear $C_{1-6}$-alkyl.

Concerning the symbols $X^1$, $X^2$, $X^3$ and $X^4$: preferably these signify independently from each other hydrogen, hydroxy or $C_{1-2}$-alkyl, more preferably they signify independently from each other hydrogen, hydroxy or methyl.

More preferred phenols are 2,3,5-trimethylhydroquinone, 2,3,6-trimethylhydroquinone 1-alkanoate, 2,3-dimethylhydroquinone, 2,5-dimethylhydroquinone, 2,6-dimethylhydroquinone, 2-methylhydroquinone and hydroquinone. Even more preferred phenols are 2,3,5-trimethylhydroquinone and 2,3,6-trimethylhydroquinone 1-alkanoate The most preferred phenols are 2,3,5-trimethylhydroquinone and 2,3,6-trimethylhydroquinone 1-acetate.

If phenols of the formula II are reacted with compounds of the formula III and/or IV, either "open ring" compounds of the formula I and/or compounds of the formula VII are obtained, depending on the activity of the catalyst, its amount and the further reaction conditions,

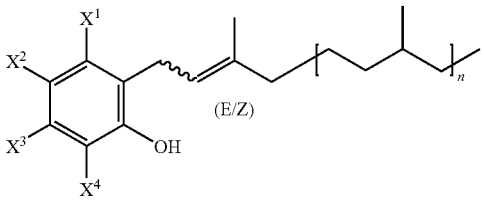

wherein $X^1$, $X^2$, $X^3$, $X^4$ and n have the same meaning and preferences as above.

Therefore, in one preferred aspect, the present invention is concerned with a process for the manufacture of compounds of alkenylated phenols of the formula I by

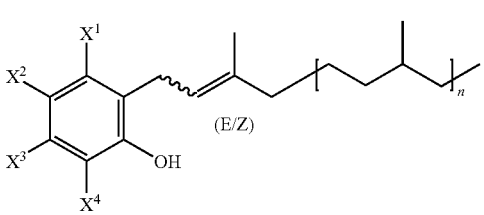

reacting a phenol of the formula II

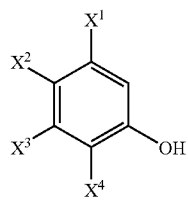
(II)

with a compound of the formula III and/or IV in an organic solvent

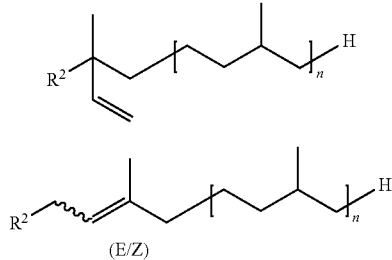
(III)
(IV)
(E/Z)

wherein $X^1$, $X^2$, $X^3$ and $X^4$ are independently from each other linear $C_{1-6}$-alkyl, hydrogen or hydroxy, $R^2$ is hydroxy, acetyloxy, benzoyloxy or halogen, n is an integer from 0 to 3, and whereby the reaction is carried out in the presence of an indium salt as the catalyst (PROCESS 1-1).

As indicated above, the "open ring" compounds of the formula I can be ring closed to obtain compounds of the formula VII. Therefore, in cases, where the activity of the catalyst, its amount or the further reaction conditions do not enable the isolation of the intermediates of the formula I the final products of the formula VII are obtained. Thus, a further preferred aspect of the present invention is a process for the manufacture of compounds of the formula VII

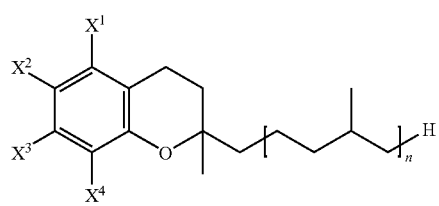
(VII)

by reacting a phenol of the formula II

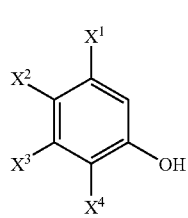
(II)

with a compound of the formula III and/or IV in an organic solvent

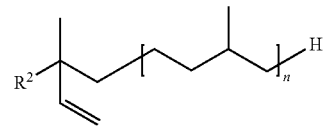
(III)

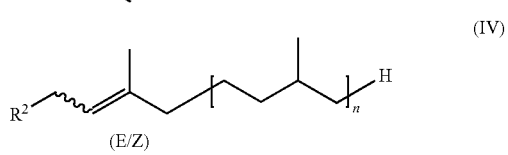
(IV)
(E/Z)

wherein $X^1$, $X^2$, $X^3$ and $X^4$ are independently from each other linear $C_{1-6}$-alkyl, hydrogen or hydroxy, $R^2$ is hydroxy, acetyloxy, benzoyloxy or halogen, n is an integer from 0 to 3, and whereby the reaction is carried out in the presence of an indium salt as the catalyst (PROCESS 1-2).

It is to be understood that PROCESS 1 encompasses PROCESS 1-1 and PROCESS 1-2.

A further object of the present invention is a process for the manufacture of compounds of the formula VII

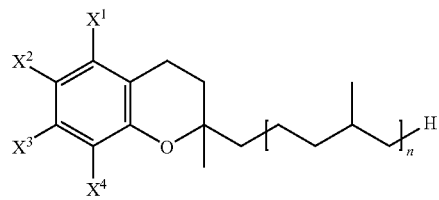
(VII)

by a) (STEP a) optionally alkenylating a phenol of the formula II

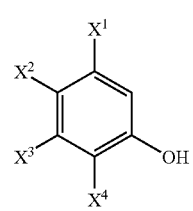
(II)

with a compound of the formula III and/or IV in an organic solvent

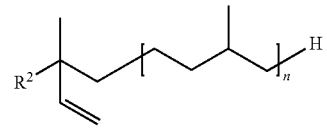
(III)

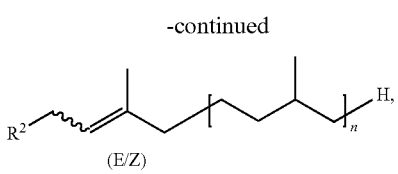

(IV)

(E/Z)

and b) (STEP b) submitting in an organic solvent a compound of the formula I

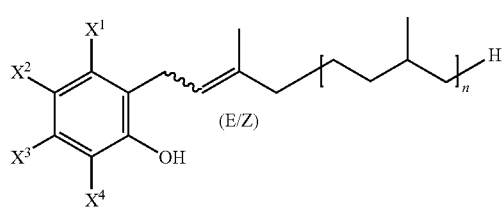

(I)

(E/Z)

and optionally one or more double bond isomers thereof, all obtainable by step a, to ring closure to form the compound of the formula VII, whereby $X^1$, $X^2$, $X^3$ and $X^4$ are independently from each other hydrogen, hydroxy or linear $C_{1-6}$-alkyl, $R^2$ is hydroxy, acetyloxy, benzoyloxy or halogen, n is an integer from 0 to 3, and at least one of the steps a and b is carried out in the presence of an indium salt as the catalyst. In the following this process will be named as PROCESS 2.

In still another aspect the invention relates to a process for the manufacture of esters of compounds selected from the group consisting of aromatic compounds featuring at least one hydroxy group (ArOH) and compounds of formula VII

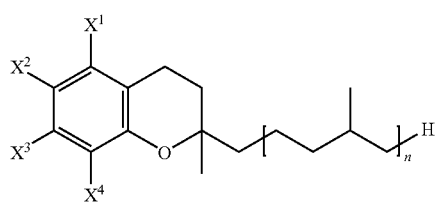

(VII)

with $X^1$, $X^2$, $X^3$ and $X^4$ being independently from each other hydrogen, hydroxy or linear $C_{1-6}$-alkyl with the proviso that at least one of the substituents $X^1$, $X^2$, $X^3$ and $X^4$ is hydroxy, with an acylating agent characterized in that the reaction is carried out in the presence of an indium salt as the catalyst (in the following referred to as PROCESS 3).

For the "aromatic compound featuring at least one hydroxy group (ArOH)" the same definition applies as given for PROCESS 1.

Suitable acylating agents will be discussed further below.

Concerning the Indium Salts Used in the Processes 1, 2 and 3 as the Catalyst:

The indium salt used as the catalyst in PROCESS 1, 2 and/or 3 is suitably an indium(III) salt. Preferably it is selected from the group consisting of indium(III) halides such as indium trichloride [$InCl_3$], indium tribromide [$InBr_3$] or indium triiodide [$InI_3$], indium tris(trifluoromethanesulfonate) (=indium(III) triflate) [$In(SO_3CF_3)_3$; $In(OTf)_3$], indium tris[bis(trifluoromethanesulfonamide)] [$In(NTf_2)_3$] and indium triacetate [$In(OAc)_3$]. More preferred is $In(OTf)_3$ or $InCl_3$.

The indium salts are known compounds which are commercially available. They can be used in solid form, anhydrous or hydrated (of which $InCl_3 \cdot 4H_2O$ is an example), as well as in solution or in suspension. Preferably the catalyst is dissolved or suspended in the organic solvent or water; for PROCESS 1 and 2 the catalyst is most preferably dissolved in water. The concentration of such a solution is not critical. Furthermore, the catalyst tolerates acetic anhydride and other acylating agents as well as protonic solvents such as acetic acid, methanol, ethanol and water. After the termination of the reaction the catalyst can be recycled.

Manufacture of the Starting Materials for the Processes 1, 2 and 3

The starting material TMHQAc may be obtained e.g. by selective hydrolysis of 2,3,5-trimethylhydroquinone diacetate as described in EP-A 1 239 045. 2,3,5-Trimethylhydroquinone diacetate can be prepared e.g. by the acid catalyzed rearrangement of ketoisophorone in the presence of acetic anhydride or another acetylation agent as described in EP-A 0 850 910, EP-A 0 916 642, EP-A 0 952 137 or EP-A 1 028 103.

The (iso)phytyl compounds can be produced by conventional processes known to the person skilled in the art. Phytol and its derivatives represented by the formula IV with n=3 can be used as E/Z-mixture as well as in pure E- or pure Z-form. Preferred is the use of phytol and its derivatives represented by the formula IV as E/Z-mixtures. The most preferred starting material selected from the (iso)phytyl compounds is IP.

Of course any other appropriate isomeric form of the (iso) phytol derivatives can also be used. (R,R)-phytol, (R,R,R)-isophytol, (S,R,R)-isophytol or (RS,R,R)-isophytol or an appropriate (iso)phytol derivative e.g. can be used to obtain (R,R)-PTMHQ/(R,R)-PTMHQA or (RS,R,R)-TCP/(RS,R,R)-TCPA, if TMHQ/TMHQA is used as the other component.

The other (di)(methyl)hydroquinones and compounds of the formula III and IV with n being 0, 1 or 2 can be prepared to processes known to the person skilled in the art.

Process 1, Step a of Process 2

The compounds obtainable by PROCESS 1 and STEP a of PROCESS 2 are alkenylated aromatic compounds featuring at least one hydroxy group. If these products have the structure of the formula I, they can further react to compounds of formula VII by a ring-closure reaction. This is dependent on the activity of the catalyst, its amount and the further reaction conditions, i.e. the reaction can proceed to the final product (compounds of formula VII) if a large amount of catalyst, a highly active catalyst and/or a high reaction temperature is employed (PROCESS 1, steps a and b of PROCESS 2) or—on the contrary—the reaction is slow enough to enable the isolation of the intermediates of the formula I (PROCESS 1, only step a of PROCESS 2 is performed).

Conveniently the reaction of the aromatic compound featuring at least one hydroxy group and a compound of the formula III and/or IV is carried out under an inert gas atmosphere, preferably gaseous nitrogen or argon. It can be carried out at atmospheric pressure or under pressure.

The reaction can be carried out batchwise or continuously, and in general operationally in a very simple manner, for example (i) by adding the compound of the formula III or IV—as such or dissolved in the non-polar solvent (if the reaction is carried out in a non-polar solvent or a two-phase solvent system) such as mentioned below, preferably as such—portionwise or continuously to a mixture of the catalyst, the aromatic compound featuring at least one hydroxy group (ArOH) and the solvent/two-phase solvent system.

It is also possible (ii) to add subsequently the catalyst, preferably as such or as aqueous solution, and the compound of the formula III or IV—as such or dissolved in the non-polar solvent (if the reaction is carried out in a non-polar solvent or a two-phase solvent system) such as mentioned below, preferably as such—to ArOH and the solvent/two-phase solvent system.

Conveniently, the compound of the formula III or IV is added continuously to ArOH within about 15 to about 180 minutes, preferably within about 30 to about 150 minutes, more preferably within about 45 to about 130 minutes, if the reaction is carried out in a single solvent, especially an aprotic non-polar solvent. If the reaction is carried out in a two-phase solvent system, the feed rate is not critical. The catalyst is preferably added at once to the mixture of ArOH and the solvent/two-phase solvent system.

After completion of the addition of the compound of the formula III or IV (in the non-polar solvent) the reaction mixture is suitably heated further at the reaction temperature for about 10 minutes to about 360 minutes, preferably for about 30 minutes to about 240 minutes. The working-up can be effected by procedures conventionally used in organic chemistry.

Suitable organic solvents for PROCESS 1 and step a of PROCESS 2 are aprotic non-polar organic solvents such as aliphatic hydrocarbons, halogenated aliphatic hydrocarbons, aromatic hydrocarbons, halogenated aromatic hydrocarbons and mixtures thereof, preferably aliphatic and aromatic hydrocarbons, as well as aprotic polar solvents such as aliphatic and cyclic carbonates, aliphatic esters and cyclic esters (lactones), aliphatic and cyclic ketones and mixtures thereof.

Preferred examples of halogenated aliphatic hydrocarbons are mono- or polyhalogenated linear, branched or cyclic $C_1$- to $C_{15}$-alkanes. Especially preferred examples are mono- or polychlorinated or -brominated linear, branched or cyclic $C_1$- to $C_{15}$-alkanes. More preferred are mono- or polychlorinated linear, branched or cyclic $C_1$- to $C_{15}$-alkanes. Most preferred are 1,1,1-trichloroethane, 1,2-dichloroethane, methylene chloride and methylene bromide.

Preferred examples of aliphatic hydrocarbons are linear, branched or cyclic $C_5$- to $C_{15}$-alkanes. Particularly preferred are linear, branched or cyclic $C_6$- to $C_{10}$-alkanes, especially preferred are hexane, heptane, octane, cyclohexane and methylcyclohexane or mixtures thereof.

Preferred examples of aromatic hydrocarbons are benzene, toluene, o-, m- and p-xylene 1,2,3-trimethylbenzene, pseudocumene, mesitylen, naphthalene and mixtures thereof.

Preferred examples of halogenated aromatic hydrocarbons are mono- or polyhalogenated benzene. Especially preferred are chlorobenzene, 1,2-dichlorobenzene, 1,3-dichlorobenzene and 1,4-dichlorobenzene.

Preferred examples of aliphatic and cyclic carbonates are ethylene carbonate, propylene carbonate and 1,2-butylene carbonate. Preferred examples of aliphatic esters and cyclic esters (lactones) are ethyl acetate, isopropyl acetate and n-butyl acetate; and γ-butyrolactone. Preferred examples of aliphatic and cyclic ketones are acetone, diethyl ketone and isobutyl methyl ketone; and cyclopentanone and isophorone. Especially preferred are cyclic carbonates and lactones, especially ethylene carbonate and propylene carbonate; and γ-butyrolactone. Most preferred are the cyclic carbonates, especially ethylene carbonate and propylene carbonate and mixtures thereof.

Two-phase solvent systems comprising polar and non-polar solvents may also be used. Examples of non-polar solvents in such two-phase solvent systems are the non-polar solvents named above. Examples of polar solvents in such two-phase solvent systems are the polar solvents named above.

The most preferred two-phase solvent systems are mixtures of ethylene carbonate and/or propylene carbonate and hexane, heptane or octane, especially mixtures of ethylene carbonate and heptane, mixtures of propylene carbonate and octane, and mixtures of ethylene carbonate, propylene carbonate and heptane.

If the reaction is carried out at atmospheric pressure, i.e. an absolute pressure of about 0.96 bar to about 1.03 bar, it is preferred to use a two-phase solvent system such as named above (with the same preferences). If the reaction is carried out under pressure, i.e. an absolute pressure of at least 1.03 bar, preferably at an absolute pressure of at least 1.1 bar, more preferably from about 1.1 to about 20.0 bar, even more preferably from about 1.1 to about 6.0 bar, then it is preferred to use an aprotic non-polar solvent such as those named above (with the same preferences). Especially preferred aprotic non-polar solvents are toluene and heptane.

The molar ratio of ArOH to the compound of the formula III and/or IV in the reaction mixture conveniently varies from about 3:1 to about 0.8:1, preferably from about 2:1 to about 1:1, more preferably from about 1.75:1 to about 1:1, if the reaction is carried out at atmospheric pressure, i.e. an absolute pressure of about 0.96 bar to about 1.03 bar.

If the reaction is carried out under pressure, i.e. at an absolute pressure of at least 1.03 bar, preferably at an absolute pressure of at least 1.1. bar, more preferably from about 1.1 bar to about 6.0 bar, even more preferably from about 1.1 bar to about 5.1 bar, even especially more preferably from about 1.7 bar to about 5.1 bar, most preferably from about 2.0 to about 3.6 bar, then the molar ratio of the ArOH to a compound represented by formula III or IV, whichever is employed, in the reaction mixture conveniently varies from about 1:1 to about 1:1.05, preferably from about 1:1.01 to about 1:1.03.

The amount of the organic solvent used is conveniently from about 0.10 ml to about 6 ml, preferably from about 0.15 ml to about 3 ml, based on 1 mmol of the compound represented by formula III or IV, whichever is employed, these amounts referring to the total amount of solvent, i.e. regardless of whether the reaction is effected in a single phase (single solvent or a homogeneous solvent mixture) or in a two-phase solvent system.

If the process is carried out in a two-phase solvent system, then the volume ratio of the non-polar solvent to the polar solvent is conveniently in the range from about 1:5 to about 30:1, preferably from about 1:3 to about 20:1, most preferably about 1:1 to about 15:1.

It has been found that the cyclic carbonate used in the two-phase solvent systems can advantageously be recycled several times.

The indium salt used as the catalyst may be present in a relative amount of from about 0.1 to about 5 mol %, preferably in a relative amount from about 0.1 mol % to about 2 mol %, more preferably in a relative amount of from about 0.1 to about 1 mol %, most preferably in a relative amount of from about 0.1 to about 0.5 mol %, based on compound III or IV, whichever is employed. In this context the expression "amount of indium salt" is to be understood as referring to the weight of pure indium salt present, even though the catalyst may be impure and/or in the hydrated form.

Suitably, the reaction temperature for the alkylation is from about 10° C. to about 160° C., preferably from about 15° C. to about 150° C., more preferably from about 20 to about 150° C., when the reaction is carried out at atmospheric pressure.

If the reaction is carried out under an absolute pressure of at least 1.03 bar, preferably of at least 1.1 bar, more preferably at an absolute pressure of from about 1.1 bar to about 20.0 bar, even more preferably at an absolute pressure of from about 1.1 to about 6.0 bar, then the reaction temperature depends on the applied pressure, but is conveniently from about 106 to about 170° C., preferably from about 112 to about 160° C. and more preferably from about 125 to about 150° C.

Step b of Process 2

This ring closure reaction can be carried out using the same catalysts under substantially the same reaction conditions as described above for the reaction of an aromatic compound featuring at least one hydroxy group (ArOH), especially a phenol of the formula II, with a compound of the formula III and/or IV. Therefore, in cases, where a compound of formula I and optionally one or more double bond isomers thereof are produced according to STEP a, it is sufficient to simply prolong the reaction time of STEP a to realize STEP b, i.e. to prolong the reaction time for about 30 minutes to about 240 minutes. Alternatively or simultaneously the amount of catalyst and/or the reaction temperature can be increased.

Process 3

According to still another aspect of this invention, a compound of formula VII, i.e. a tocopherol, e.g. α-tocopherol or γ-tocopherol, or any other tocol derivative as described in DE-OS 21 60 103 on page 5 in the third and forth paragraph, and an aromatic compound featuring at least one hydroxy group (ArOH) as defined above may be converted into its ester, e.g., its acetate by treatment with an acylating agent in the presence of an indium salt.

The acylation in accordance with that aspect of the invention can be carried out using acylating agents conventionally used in the acylation of tocopherols such as anhydrides or halides.

Examples of these are anhydrides or halides of alkanoic acids such as acetic acid, propionic acid, pivalic acid, palmitic acid, nicotinic acid and succinic acid. Typically, acetic anhydride or acid chloride, especially acetic anhydride, is used.

The molar ratio of the aromatic compound featuring at least one hydroxy group (ArOH) or the compound of formula VII to the acylating agent in the reaction mixture conveniently varies from about 1:0.8 to about 1:5, preferably from about 1:1 to about 1:3, more preferably from about 1:1.1 to about 1:2.

The amount of catalyst used is based on the lesser molar amount of reactant, i.e. ArOH/compound of formula VII or acylating agent, and can be in the range of from about 0.006 mol % to about 2.0 mol %, preferably from about 0.0075 mol % to about 1.5 mol %, more preferably from about 0.01 mol % to about 1.0 mol %, in the batchwise mode of operation. For continuous operation, the amount of catalyst will be adjusted to the size of the reactor and the flow of the reactants. It will be appreciated that the determination of the appropriate figures based on the figures for batchwise operation is within normal skill.

The acylation reaction can preferably be carried out at temperatures below about 120° C., more preferably at temperatures from about 15° C. to about 120° C., most preferably at temperatures from about 15° C. to about 40° C.

The reaction can be carried out essentially in the absence of an additional organic solvent, which is preferred.

"Essentially in the absence of an additional organic solvent" in the context of the present invention means that essentially no organic solvent is present during the reaction and that no organic solvent is deliberately added. It might, however, be possible that traces of organic solvent are present in the starting materials or the catalyst as impurities. In other words, the reaction is carried out in substance; i.e. no other compound except ArOH/compound of formula VII, acetic anhydride and the catalyst is intendedly used for the reaction, so that at the beginning of the reaction the amount of any substance except for the starting material, ArOH/compound of formula VII and acetic anhydride, and except for the catalyst in the reaction mixture is ≦5 weight %, preferably ≦3 weight %, more preferably ≦0.5 weight %, and that no further compound is added during the reaction.

The reaction is conveniently carried out under an inert gas atmosphere, preferably gaseous nitrogen or argon.

The reaction is conveniently carried out at an absolute pressure of at least 0.02 bar, preferably at an absolute pressure of from about 0.02 to about 10.0 bar, more preferably at an absolute pressure of from about 0.02 bar to about 6.0 bar, even more preferably at an absolute pressure of from about 0.1 bar to about 5 bar, most preferably at an absolute pressure of from about 0.2 bar to about 3 bar.

It is a particular feature of the acylation according to the present invention that when using chiral aromatic compounds featuring at least one hydroxy group or tocol and tocopherols, e.g. (enantiomeric pure) (R,R,R)-γ-tocopherol (formula VII with $X^1$=H, $X^2$=OH, $X^3$=$X^4$=methyl and n=3), the acylation proceeds substantially without epimerization.

PREFERRED EMBODIMENTS OF THE INVENTION

Preferred Embodiments of Process 1

Preferred is a process for the manufacture of 2-phytyl-3,5, 6-trimethylhydroquinone or 3-phytyl-2,5,6-trimethylhydroquinone 1-alkanoates (both represented by formula Ia with n=3)

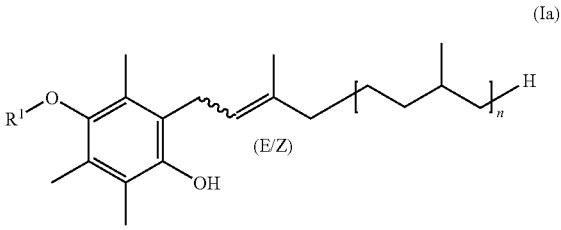

(Ia)

by reacting 2,3,5-trimethylhydroquinone or 2,3,6-trimethylhydroquinone 1-alkanoate (both represented by formula IIa)

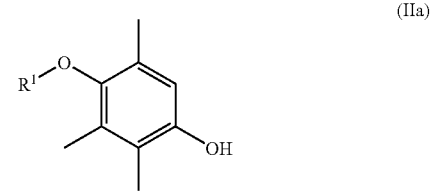

(IIa)

with a compound of the formula IIIa and/or IVa, both with n=3, in an organic solvent

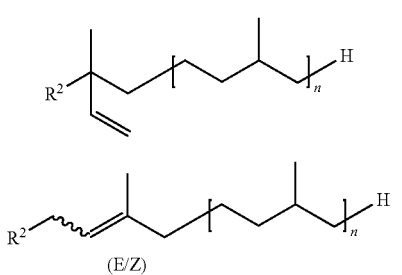

whereby $R^1$ is hydrogen, acetyl, propionyl, pivaloyl, $HO_2C-CH_2-CH_2-CO$, nicotinoyl or palmityl, $R^2$ is hydroxy, acetyloxy, benzoyloxy or halogen, and n is 3, and whereby the reaction is carried out in the presence of an indium salt as the catalyst. In the following this process will be named as PROCESS 1A.

Concerning the symbol $R^1$ of the compounds of the formulae IIa and Ia: preferably it signifies hydrogen or acetyl, more preferably it is hydrogen.

Concerning the moiety $R^2$ of the compounds of the formulae IIIa and/or IVa: preferably $R^2$ is hydroxy, acetyloxy, benzoyloxy, chlorine or bromine, more preferably $R^2$ is hydroxy, acetyloxy or chlorine, most preferably $R^2$ is hydroxy.

While in PROCESS 1A of the present invention the production of (all-rac)-PTMHQ or (all-rac)-PTMHQA, especially (all-rac)-PTMHQAc is preferred, the invention is not limited to the production of that particular isomeric form and other isomeric forms can be obtained by using phytol, isophytol or a derivative thereof as the starting material in the appropriate isomeric form. Thus, (R,R)-PTMHQ or (R,R)-PTMHQA will be obtained when using (R,R)-phytol, (R,R,R)-isophytol, (S,R,R)-isophytol or (RS,R,R)-isophytol or an appropriate (iso)phytol derivative.

Depending on the activity of the catalysts, its amount and the further reaction conditions the intermediates of the formula Ia may not be isolated but react further to the final product of the formula VIIa, α-tocopherol or its alkanoate. Therefore PROCESS 1A also embraces a process (designated PROCESS 1A-2) for the manufacture of α-tocopherol or its alkanoates (both represented by formula VIIa)

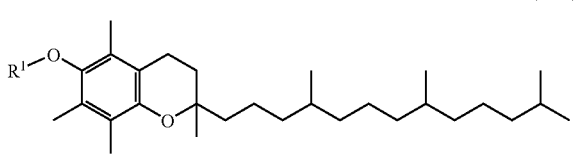

by reacting 2,3,5-trimethylhydroquinone or 2,3,6-trimethylhydroquinone 1-alkanoate (both represented by formula IIa)

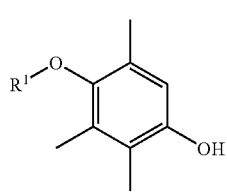

with a compound of the formula IIIa and/or IVa, both with n=3, in an organic solvent

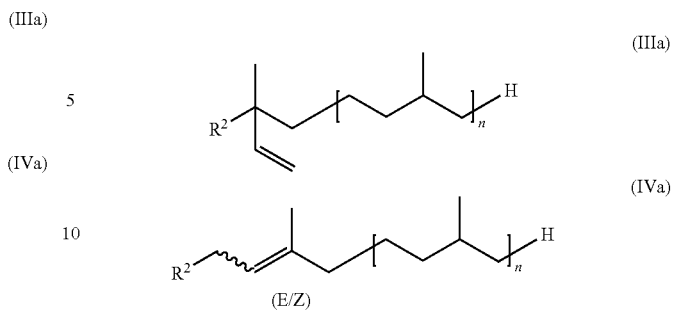

whereby $R^1$, $R^2$ and n have the same meanings and preferences as described for PROCESS 1A, and whereby the reaction is carried out in the presence of an indium salt as the catalyst.

Preferred Embodiments of Process 2

In this aspect, the present invention is concerned with a process for the manufacture of α-tocopherol or its alkanoates by a) (STEP a) optionally reacting 2,3,5-trimethylhydroquinone or 2,3,6-trimethylhydroquinone 1-alkanoates (both represented by formula IIa)

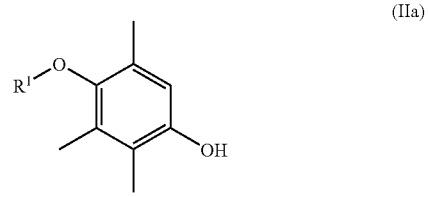

with a compound of the formula IIIa and/or IVa, both with n=3, in an organic solvent

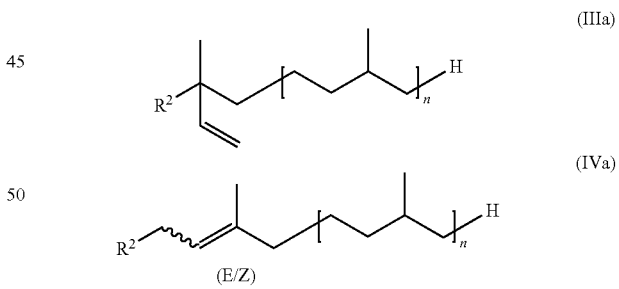

with $R^1$, $R^2$ and n having the same meaning and preferences as above for PROCESS 1A and b) (STEP b) submitting in an organic solvent 2-phytyl-3,5,6-trimethylhydroquinone or 3-phytyl-2,5,6-trimethylhydroquinone 1-alkanoates and optionally one or more isomers thereof, all obtainable by STEP a, to ring closure to form α-tocopherol or its alkanoates, whereby at least one of the steps a and b is carried out in the presence of an indium salt as the catalyst. To this process it will be referred to in the following as PROCESS 2A.

While in PROCESS 2A of the present invention the production of (all-rac)-α-tocopherol (formula VIIa with $R^1$=hydrogen) or (all-rac)-α-tocopheryl alkanoate (formula VIIa with $R^1$=acetyl, propionyl, pivaloyl, $HO_2C$—$CH_2$—$CH_2$—CO, nicotinoyl or palmityl), especially (all-rac)-α-tocopheryl acetate (formula VIIa with $R^1$=acetyl) is preferred, the invention is not limited to the production of that particular isomeric form and other isomeric forms can be obtained by using phytol, isophytol or a derivative thereof as the starting material in the appropriate isomeric form. Thus, e.g. (RS,R,R)-α-tocopherol/(RS,R,R)-α-tocopheryl acetate will be obtained when using (R,R)-PTMHQ or (R,R)-PTMHQAc or (R,R)-phytol, (R,R,R)-isophytol, (S,R,R)-isophytol or (RS,R,R)-isophytol or an appropriate (iso)phytol derivative.

In an especially preferred embodiment of the invention 2,3,5-trimethylhydroquinone is reacted with phytol (formula IVa with $R^2$=OH and n=3) and/or isophytol (formula IIIa with $R^2$=OH and n=3), preferably with isophytol, to α-tocopherol, whereby as the intermediates 2-phytyl-3,5,6-trimethylhydroquinone (formula Ia; as the main component), 3-(3,7,11,15-tetramethyl-hexadec-3-enyl)-2,5,6-trimethylhydroquinone (formula Va with $R^1$=H) and 3-[3-(4,8,12-trimethyl-tridecyl)-but-3-enyl]-2,5,6-trimethylhydroquinone (formula VIa with $R^1$=H) are formed.

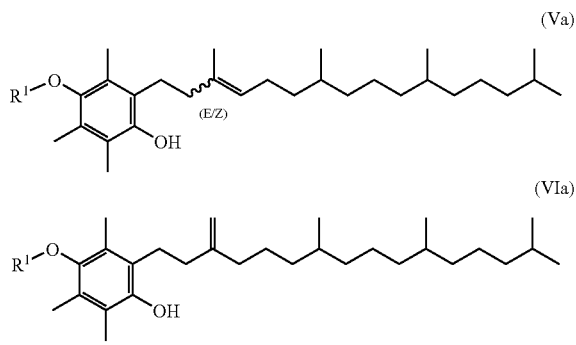

(Va)

(VIa)

Preferred Embodiments of Process 3

In this aspect the invention relates to a process for the manufacture of α-tocopheryl alkanoates (represented by formula VIII),

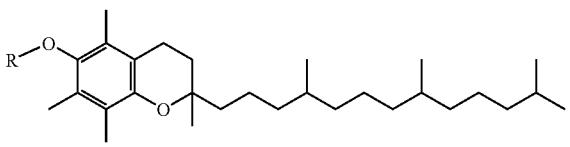

(VIII)

by reacting α-tocopherol (represented by formula VIIb)

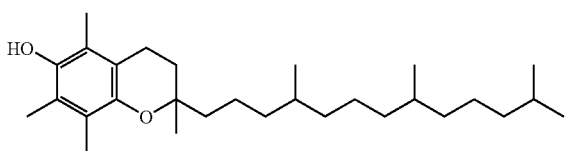

(VIIb)

with an acylating agent characterized in that the reaction is carried out in the presence of an indium salt as the catalyst (in the following referred to as PROCESS 3A).

Concerning the substituent R: preferably R is acetyl, propionyl, pivaloyl, palmityl, $HO_2C$—$CH_2$—$CH_2$—CO or nicotinoyl, more preferably R is $HO_2C$—$CH_2$—$CH_2$—CO or acetyl, most preferably R is acetyl.

While in an especially preferred embodiment of PROCESS 3A of the present invention (all-rac)-α-tocopheryl alkanoate (formula VIII; see above), especially (all-rac)-α-tocopheryl acetate (formula VIII with R=acetyl) is produced, the invention is not limited to the production of that particular isomeric form and other isomeric forms can be obtained by using phytol, isophytol or a derivative thereof as the starting material in the appropriate isomeric form. Thus, (R,R,R)-α-tocopheryl alkanoate/acetate will be obtained when using (R,R,R)-α-tocopherol as starting material, since no epimerization occurs under the reaction conditions.

In a preferred embodiment the (all-rac)-α-tocopherol obtained by PROCESS 2A is acetylated after removal of the solvent without further purification with acetic anhydride at room temperature in a short reaction time (up to 10 minutes) and with total conversion. No additional catalyst needs to be used as the indium salt is still present. After acetylation (all-rac)-α-tocopheryl acetate has been isolated in excellent yield [>99.5% based on (all-rac)-α-tocopherol].

Concerning the Indium Salts Used in the Preferred Embodiments the Processes 1A, 2A and 3A as the Catalyst:

$In(OTf)_3$ is especially preferred for the acylation of α-tocopherol (PROCESS 3A) and the reaction of TMHQ or TMHQA with a compound represented by formula IIIa and/or IVa (PROCESS 1A or STEP a of PROCESS 2A), if carried out in a two-phase solvent system. $InCl_3$ is the most preferred catalyst if the reaction of TMHQ or TMHQA with a compound represented by formula IIIa and/or IVa (PROCESS 1A or STEP a of PROCESS 2A) is carried out in a single phase solvent system.

For PROCESS 1A and 2A the catalyst is most preferred dissolved in water. The concentration of such a solution is not critical.

Process 1A, Step a of Process 2A

As will be readily apparent, the use of TMHQ as a reactant in this process of the present invention will result in the production of PTMHQ while, when using TMHQA, especially TMHQAc, the respective PTMHQA/PTMHQAc will be obtained.

As by-products minor amounts of the isomers of PTMHQ (A), (Z)- or(E)-2,3,6-trimethyl-5-(3,7,11,15-tetramethyl-hexadec-3-enyl)hydroquinone (1-alkanoate) (represented by the formula Va; see above) and/or 2,3,6-trimethyl-5-[3-(4,8,12-trimethyl-tridecyl)-but-3-enyl]hydroquinone (1-alkanoate) (represented by the formula VIa; see above) may be formed in PROCESS 1A as well as in STEP a of PROCESS 2A.

PTMHQ(A) and its isomers represented by the formulae Va and VIa are intermediates for the production of α-tocopherol or its alkanoates (final products).

Depending on the activity of the catalyst, its amount and the further reaction conditions, the reaction proceeds to the final product α-tocopherol (alkanoate) (STEPS a and b of PROCESS 2A) or is slow enough so that these intermediates of the formula Ia can be isolated (only STEP a of PROCESS 2A is performed).

Preferably TMHQ is reacted with PH and/or IP, more preferably with IP.

Conveniently the reaction of TMHQ(-1-alkanoate) and a compound of the formula IIIa and/or a compound of the formula IVa is carried out under an inert gas atmosphere, preferably gaseous nitrogen or argon. It can be carried out at atmospheric pressure or under pressure.

The reaction can be carried out batchwise or continuously, and in general operationally in a very simple manner, for example (i) by adding the compound represented by formula IIIa or IVa—as such or dissolved in the non-polar solvent (if the reaction is carried out in a non-polar solvent or a two-phase solvent system) such as mentioned below, preferably as such—portionwise or continuously to a mixture of the catalyst, TMHQ or its 1-alkanoates and the solvent/two-phase solvent system.

It is also possible (ii) to add subsequently the catalyst, preferably as such or as aqueous solution, and the compound represented by the formula IIIa or IVa—as such or dissolved in the non-polar solvent (if the reaction is carried out in a non-polar solvent or a two-phase solvent system) such as mentioned below, preferably as such—to TMHQ or its 1-alkanoates and the solvent/two-phase solvent system.

Conveniently, the compound of the formula IIIa and/or IVa is added continuously to TMHQ or its 1-alkanoates within about 15 to about 180 minutes, preferably within about 30 to about 150 minutes, more preferably within about 45 to about 130 minutes, if the reaction is carried out in a single solvent, especially an aprotic non-polar solvent. If the reaction is carried out in a two-phase solvent system, the feed rate is not critical. The catalyst is preferably added at once to the mixture of TMHQ or its 1-alkanoates and the solvent/two-phase solvent system having already reached the reaction temperature.

After completion of the addition of the compound represented by formula IIIa or IVa (in the non-polar solvent) the reaction mixture is suitably heated further at the reaction temperature for about 10 minutes to about 360 minutes, preferably for about 30 minutes to about 240 minutes. The working-up can be effected by procedures conventionally used in organic chemistry.

Suitably, the reaction temperature for the alkylation is from about 10° C. to about 160° C., preferably from about 15° C. to about 150° C., more preferably from about 20° C. to about 150° C., when the reaction is carried out at atmospheric pressure.

If the reaction is carried out under pressure, i.e. at an absolute pressure of at least 1.03 bar, preferably at an absolute pressure of at least 1.1 bar, more preferably at an absolute pressure of from about 1.1 to about 20.0 bar, even more preferably at an absolute pressure of from about 1.1 to about 6.0 bar, then the reaction temperature depends on the applied pressure, but is conveniently from about 106 to about 170° C., preferably from about 112 to about 160° C. and more preferably from about 125 to about 150° C.

If the reaction is carried out under pressure, i.e. at an absolute pressure of at least 1.03 bar, preferably an aprotic non-polar organic solvent such as an aliphatic hydrocarbon, a halogenated aliphatic hydrocarbon, an aromatic hydrocarbon, a halogenated aromatic hydrocarbon and mixtures thereof are used. Examples and their preferences are the same as given above for PROCESS 1 and step a of PROCESS 2.

If the reaction is carried out at atmospheric pressure, i.e. a pressure of from about 0.96 bar to about 1.03 bar, the reaction is preferably carried out in a two-phase solvent system comprising polar and non-polar solvents. Examples of non-polar solvents and polar solvents in such two-phase solvent systems and their preferences are the same as named above for PROCESS 1 or step a of PROCESS 2.

The molar ratio of TMHQ or its 1-alkanoates to a compound represented by formula IIIa and/or IVa in the reaction mixture conveniently varies from about 3:1 to about 0.8:1, preferably from about 2:1 to about 1:1, more preferably from about 1.75:1 to about 1:1, if the reaction is carried out at atmospheric pressure, i.e. an absolute pressure of about 0.96 bar to about 1.03 bar.

If the reaction is carried out under pressure, i.e. at an absolute pressure of at least 1.03 bar, preferably of at least 1.1 bar, more preferably at an absolute pressure of from about 1.1 bar to about 6.0 bar, even more preferably from about 1.1 bar to about 5.1 bar, even especially more preferably from about 1.7 bar to about 5.1 bar, most preferably from about 2.0 to about 3.6 bar, then the molar ratio of TMHQ or its 1-alkanoates to a compound represented by formula IIIa and/or IVa, whichever is employed, in the reaction mixture conveniently varies from about 1:1 to about 1:1.05, preferably from about 1:1.01 to about 1:1.03.

The amount of organic solvent used is conveniently from about 0.10 ml to about 6 ml, preferably from about 0.15 ml to about 3 ml, based on 1 mmol of the compound represented by formula IIIa or IVa, whichever is employed, these amounts referring to the total amount of solvent, i.e. regardless of whether the reaction is effected in a single phase (single solvent or a solvent mixture) or in a two-phase solvent system.

If the process is carried out at atmospheric pressure and in a two-phase solvent system, then the volume ratio of the non-polar solvent to the polar solvent is conveniently in the range from about 1:5 to about 30:1, preferably from about 1:3 to about 20:1, most preferably about 1:1 to about 15:1.

It has been found that the cyclic carbonate used in the two-phase solvent systems can advantageously be recycled several times.

The indium salt used as the catalyst may be present in a relative amount of from about 0.1 to about 5 mol %, preferably in a relative amount from about 0.1 mol % to about 2 mol %, more preferably in a relative amount of from about 0.1 to about 1 mol %, most preferably in a relative amount of from about 0.1 to about 0.5 mol %, based on compound IIIa or IVa, whichever is employed. In this context the expression "amount of indium salt" is to be understood as referring to the weight of pure indium salt present, even though the catalyst may be impure and/or in the hydrated form.

Step b of Process 2A

As will be readily apparent, the use of PTMHQ or an isomer thereof as a reactant in the process of this invention will result in the preparation of α-tocopherol while, when using a PTMHQA or an isomer thereof, the respective α-tocopheryl alkanoate will be obtained.

As the starting material PTMHQ or PTMHQA and optionally one or more isomers thereof, which are obtained as minor by-products in the manufacture of PTMHQ or PTMHQA, prepared to any method known to the person skilled in the art can be used.

This ring closure can be carried out using the same catalysts under substantially the same reaction conditions as described above for the reaction of TMHQ or TMHQA represented by formula Ia with a compound of the formula IIIa and/or IVa. Therefore, in cases, where PTMHQ or PTMHQA and optionally one or more isomers thereof are produced according to STEP a, it is sufficient to simply prolong the reaction time of STEP a to realize STEP b, i.e. to prolong the reaction time for about 30 minutes to about 240 minutes. Alternatively or simultaneously the amount of catalyst and/or the reaction temperature can be increased.

Process 3A

According to still another aspect of this invention, α-tocopherol may be converted into its alkanoate, e.g. its acetate, by treatment with an acylating agent in the presence of an indium salt.

The acylation in accordance with that aspect of the invention can be carried out under the same reaction conditions as already described for PROCESS 3.

It is a particular feature of the acylation according to the present invention that when using (R,R,R)-α-tocopherol, the acylation proceeds substantially without epimerization. Thus, if for example (R,R,R)-α-tocopherol is used as starting material for PROCESS 3A, (R,R,R)-α-tocopheryl alkanoate is obtained.

Process 4

According to sill another aspect of this invention, α-tocopherol, β-tocopherol, γ-tocopherol and δ-tocopherol as defined in DE-OS 21 60 103 (page 5, third paragraph) and obtained according to the process of the present invention may be converted into their alkanoates, e.g. their acetates, by treatment with an acylating agent.

The acylation in accordance with that aspect of the invention can be carried out according to processes already known by the person skilled in the art.

Process for the Manufacture of Formulations of α-Tocopherol or its Alkanoates

The α-tocopherol or its alkanoate obtained by one of the PROCESSES 1, 2, 3, 3A or 4 can further be formulated by any method known to the person skilled in the art, e.g. as those disclosed in U.S. Pat. No. 6,162,474, U.S. 2001/0009679, U.S. Pat. No. 6,180,130, U.S. Pat. No. 6,426,078, U.S. Pat. No. 6,030,645, U.S. Pat. No. 6,150,086, U.S. Pat. No. 6,146,825, U.S. Pat. No. 6,001,554, U.S. Pat. No. 5,938,990, U.S. Pat. No. 6,530,684, U.S. Pat. No. 6,536,940, U.S. Pat. 2004/0053372, U.S. Pat. No. 5,668,183, U.S. Pat. No. 5,891,907, U.S. Pat. No. 5,350,773, U.S. Pat. No. 6,020,003, U.S. Pat. No. 6,329,423, WO 96/32949, U.S. Pat. No. 5,234,695, WO 00/27362, EP 0 664 116, U.S. 2002/0127303, U.S. Pat. No. 5,478,569, U.S. Pat. No. 5,925,381, U.S. Pat. No. 6,651,898, U.S. Pat. No. 6,358,301, U.S. Pat. No. 6,444,227, WO 96/01103 and WO 98/15195.

Use of the Indium Salts Named Above

The present invention is also directed to the use of the indium salts named above in the processes according to the present invention, the PROCESSES 1, 1-1,1-2, 1A, 1A-1, 2, 2A, 3 and 3A. Especially the present invention relates to the use of an indium salt as the catalyst in a Friedel-Crafts alkylation reaction of aromatic compounds featuring at least one hydroxy group in an organic solvent, as well as to the use of an indium salt as the catalyst in ring-closure reactions to produce chroman-ring compounds in an organic solvent.

The following Examples illustrate the invention further.

EXAMPLES

In the following examples minor amounts of the following by-products were obtained:

PTMQ: phytyltrimethylquinone:

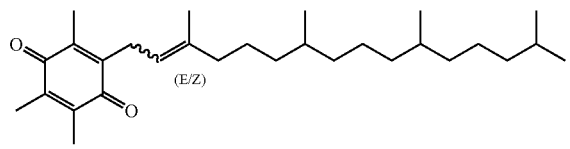

PTD: phytadienes=dehydrated by-products of IP (easily separable);

DHTC: 3,4-dehydro-α-tocopherol

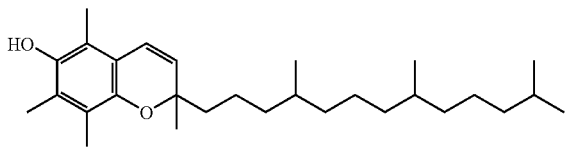

BZF: benzofuranes:

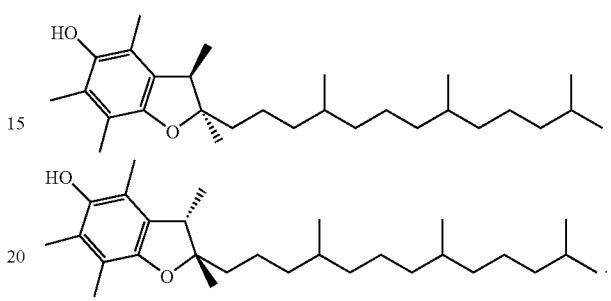

Phytyl-toluene compounds and their double-bond isomers (easily separable):

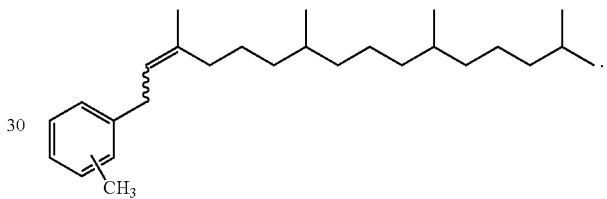

The analysis of the products was done by gas chromatography (GC) using an internal standard.

Jeffsol EC50® is a solvent mixture available from Huntsman Corp., PO Box 15730 Austin, Tex., USA/Antwerp 2030, Belgium, which consists of ethylene carbonate and propylene carbonate in the volume ratio 1:1.

If examples were carried out at "atmospheric pressure", this has indicates that the reaction was carried out at a pressure from about 0.96 bar to about 1.03 bar.

Examples 1-14

Preparation of PTMHQ

Examples 1-3

$InCl_3$ as the Catalyst 12.88 mmol of TMHQ and 8.58 mmol of IP were reacted in the solvent or solvent system given in Table 1 in the presence of $InCl_3$ as the catalyst (amounts of the catalyst given in Table 1) and at atmospheric pressure. The reaction time was 2 hours. For further details and the results see Table 1.

Examples 4 and 5

$In(OTf)_3$ as the Catalyst 12.88 mmol of TMHQ and 8.58 mmol of IP were reacted in a mixture of 20 ml of heptane and 20 g of Jeffsol EC 50® in the presence of increasing amounts (see Table 1) of $In(OTf)_3$ as the catalyst and at atmospheric pressure. For further details about the reaction conditions and the results see Table 1.

TABLE 1

The amount of THMQ was 12.88 mmol in all cases,
the amount of IP was 8.58 mmol in all cases.

| Example | Catalyst | Amount of catalyst [mol %] | Solvent | Reaction temperature | Reaction time [hour(s)] | Yield of PTMHQ [%] - based on IP |
|---|---|---|---|---|---|---|
| 1 | $InCl_3$ | 0.1 | 20 ml of Jeffsol EC50 ® + 20 ml of heptane | 94° C. | 2 | 47.2 |
| 2 | $InCl_3$ | 2.0 | 20 g of butyl acetate | reflux | 2 | 60.2 |
| 3 | $InCl_3$ | 2.0 | 20 g of diethylketone | reflux | 2 | 80.3 |
| 4 | $In(OTf)_3$ | 0.01 | 20 ml of Jeffsol EC50 ® + 20 ml of heptane | 94° C. | 12 | 58.7 |
| 5 | $In(OTf)_3$ | 1.0 | 20 ml of Jeffsol EC50 ® + 20 ml of heptane | 22° C. | 100.5 | 90.5 |

Examples 6 and 7

$InCl_3$ as the Catalyst

Varying amounts of TMHQ were reacted with 17.17 mmol of IP in 45 ml of toluene at 110° C. in the presence of 1.0 mol % of $InCl_3$—based on IP—as the catalyst and at atmospheric pressure. Further details and the results are presented in Table 2.

Example 8

$In(OTf)_3$ as the Catalyst

TMHQ (38.63 mmol) and IP (25.75 mmol, 97%, added during 1 hour) were reacted in a molar ratio of 1.5:1 in the presence of 1.0 mol % of $In(OTf)_3$ as the catalyst (amount based on IP) at 22° C. and at atmospheric pressure. For further details and the results see Table 2. After separation of the heptane phase, and washing of the heptane phase with Jeffsol 50® (60 ml), the resulting mixture (suspension in heptane) was filtered under vacuum. The pasty nearly colorless solid was analysed by GC.

Example 9

$In(OTf)_3$ as the Catalyst

TMHQ (24.691 g, 161.1 mmol) and IP (38.833 ml, 107.4 mmol, 97%, added during 1 hour) were reacted in a molar ratio of 1.5:1 in the presence of 1.0 mol % of $In(OTf)_3$ as the catalyst (amount based on IP) at 22° C. and at atmospheric pressure. For further details and the results see Table 2. After separation of the heptane phase and washing of the heptane phase with Jeffsol EC50® (250 ml) the resulting suspension in heptane was filtered under vacuum. The pasty nearly colorless solid was analysed by quantitative GC.

TABLE 2

The amount of catalyst was 1.0 mol % - based on IP - in all cases.

| | Example | | | |
|---|---|---|---|---|
| | 6 | 7 | 8 | 9 |
| Amount of TMHQ [mmol] | 17.17 | 25.76 | 38.63 | 161 |
| Amount of IP [mmol] | 17.17 | 17.17 | 25.75 | 107 |
| Catalyst | $InCl_3$ | $InCl_3$ | $In(OTf)_3$ | $In(OTf)_3$ |
| Solvent | Toluene | Toluene | 60 ml of Jeffsol EC50 ® + 60 ml of heptane | 250 ml of Jeffsol EC50 ® + 250 ml of heptane |
| Reaction temperature | 110° C. | 110° C. | 22° C. | 22° C. |
| Reaction time [h] | 10 | 2 | 92 | 192 |
| Yield of PTMHQ - based on IP | 63.9 | 73.6 | 88.7 | 59.7 |

Examples 10-14

200 mmol of TMHQ were reacted with 200 mmol of IP (examples 10 and 13) and 203 mmol of IP (examples 11, 12 and 14), respectively, in the presence of increasing amounts of $In(OTf)_3$ (example 10) or $InCl_3$ (examples 11-14) as the catalyst in 100 ml of an organic solvent. Examples 10 and 14 were carried out under pressure, whereby examples 11-13 were carried out at atmospheric pressure. For the reaction temperature, the pressure, the reaction time and the type of solvent see Table 3.

TABLE 3

The amount of solvent was 100 ml in all cases. The amount of TMHQ was 200 mmol in all cases. In the examples 11, 12 and 14 a molar excess of IP of 1.5 mol% based on the amount of TMHQ was used. The yield of PTMHQ is based on IP.

| Example | Amount of IP [mmol] | Catalyst and its amount [mol %] | | Solvent | Reaction temperature | Pressure [bar] | Reaction time | Yield of PTMHQ [%] |
|---|---|---|---|---|---|---|---|---|
| 10 | 200 | 0.001 | In(OTf)$_3$ | Toluene | 137° C. | 2 | 3 hours | 35.0 |
| 11 | 203 | 0.25 | InCl$_3$ | Heptane | 98° C. | 1 | 4 hours | 61.2 |
| 12 | 203 | 0.5 | InCl$_3$ | Heptane | 98° C. | 1 | 3 hours | 48.8 |
| 13 | 200 | 1.0 | InCl$_3$ | Heptane | 98° C. | 1 | 2 hours | 43.4 |
| 14 | 203 | 2.0 | InCl$_3$ | CH$_2$Cl$_2$ | 40° C. + 86° C. | 4 | 23 hours + 22 hours | 52.9 |

Examples 15-18

Preparation of (all-rac)-TCP in a Two-Phase Solvent System with InCl$_3$ as the Catalyst In a 100 ml four-necked flask equipped with a mechanical stirrer, a thermometer, a Dean-Stark separator, and a reflux condenser, 2.00 g (12.878 mmol) of TMHQ (purity 98%), 2.0 mol % of InCl$_3$ (based on IP) and certain amounts of a two-phase solvent system (see Table 4) were heated under argon atmosphere to reflux (oil bath 140 to 145° C.). 3.106 ml (8.585 mmol) of IP (purity 97%) were added at a rate of 0.052 ml per minute within 1 hour. Approximately 0.15 ml water were collected after complete addition of IP. After 20 minutes of stirring heptane was distilled off within approximately 10 minutes. Afterwards the reaction mixture was heated for 1 hour at 125 to 130° C. The reaction mixture was cooled to 80° C. and 40 ml of heptane were added to the carbonate phase. The reaction mixture was stirred for additional 20 minutes at 60° C. The heptane layer was separated and the carbonate phase was extracted with heptane (40 ml). The combined heptane phases were evaporated under reduced pressure. TCP was obtained as a viscous oil. For the yields—based on IP—see Table 4.

Examples 19-20

Preparation of (all-rac)-TCP in a Single Phase Solvent with InCl$_3$ as the Catalyst In a 100 ml four-necked flask equipped with a mechanical stirrer, a thermometer, a Dean-Stark separator, and a reflux condenser, 2.00 g (12.878 mmol) of TMHQ, 2.0 mol % of InCl$_3$ (based on IP), 20 ml of solvent (diethyl ketone or butyl acetate) were heated up under argon atmosphere to reflux (oil bath 140 to 145° C.). 3.106 ml (8.585 mmol) of IP were added at a rate of 0.052 ml per minute within 1 hour. After complete addition of IP the reaction mixture was heated for 4 hours at 103° C. (oil bath 140 to 145° C.). The reaction mixture was cooled down and was concentrated under reduced pressure to give (all-rac)-TCP. The yields—based on IP—are given in Table 4.

Examples 21-22

Preparation of (all-rac)-TCP in a Single Phase Solvent with In(OTf)$_3$ as the Catalyst Example 15 was repeated but instead of InCl$_3$ In(OTf)$_3$ was used as the catalyst and the reaction was carried out in a single solvent.

TABLE 4

Reaction of TMHQ with IP in the presence of InCl$_3$ (examples 15-20) or In(OTf)$_3$ (examples 21-22)

| Example | Solvent | Reaction Time [hour(s)] | Yield of PTMHQ [%] - based on IP | Yield of TCP [%] - based on IP |
|---|---|---|---|---|
| 15 | 10 ml of propylene carbonate + 10 ml of heptane | 1 | 0.36 | 88.9 |
| 16 | 10 ml of ethylene carbonate + 10 ml heptane | 1 | 0.12 | 98.1 |
| 17 | 20 ml of ethylene carbonate/ propylene carbonate (v/v = 1/1) + 20 ml of heptane | 1 | 0.77 | 90.5 |
| 18 | 10 ml of γ-butyrolactone + 10 ml heptane | 4 | 0.23 | 83.5 |
| 19 | 20 ml of diethylketone | 4 | 0.37 | 95.1 |
| 20 | 20 ml of butyl acetate | 4 | 4.67 | 80.6 |
| 21 | 20 ml of toluene | 1 | 0 | 78.9 |
| 22 | 20 ml of heptane | 1 | 2.48 | 80.2 |

Examples 23-25

Influence of the Amount of $InCl_3$ as the Catalyst

Example 16 was repeated but the amount of $InCl_3$ as well as the reaction time was varied. The results are presented in Table 5.

TABLE 5

Reaction of TMHQ with IP in a solvent system consisting of 10 ml of ethylene carbonate and 10 ml of heptane in the presence of varying amounts of $InCl_3$.

| Example | Amount of $InCl_3$ [mol %] - based on IP | Reaction time [hours] | Yield of PTMHQ [%] - based on IP | Yield of TCP [%] - based on IP |
|---|---|---|---|---|
| 16 | 2.0 | 1 | 0.12 | 98.1 |
| 23 | 0.1 | 4 | 2.33 | 94.8 |
| 24 | 0.5 | 1 | 0.19 | 96.0 |
| 25 | 1.0 | 1 | 0 | 95.1 |

Examples 26-31

Use of Different Indium Salts

Example 16 was repeated but the amount and type of catalyst was varied. In the examples 26-29 and 31 12.878 mmol of TMHQ and 8.858 mmol of IP were reacted with each other, whereby in example 30 8.858 mmol of TMHQ and 8.858 mmol of IP were used. The results are summarized in Table 6.

TABLE 6

Reaction of TMHQ with IP in a solvent system consisting of 10 ml of ethylene carbonate and 10 ml of heptane in the presence of varying amounts of different indium salts.

| Example | Catalyst | Amount of catalyst [mol %] - based on IP | Reaction time [hour(s)] | Yield of PTMHQ [%] - based on IP | Yield of TCP [%] - based on IP |
|---|---|---|---|---|---|
| 16 | $InCl_3$ | 2 | 1 | 0.12 | 98.1 |
| 23 | $InCl_3$ | 0.1 | 4 | 2.33 | 94.8 |
| 26 | $InI_3$ | 2 | 1 | 0.25 | 97.3 |
| 27 | $InBr_3$ | 2 | 1 | 0.15 | 93.1 |
| 28 | $In(OTf)_3$ | 2 | 1 | 0 | 99.1 |
| 29 | $In(OTf)_3$ | 0.1 | 1 | 0.37 | 91.6 |
| 30 | $In(OTf)_3$ | 0.1 | 1 | 0.10 | 93.9 |
| 31 | $In(OAc)_3$ | 2 | 1 | 0.50 | 0.13 |

Example 32-34

Preparation of (all-rac)-TCPA

In a 100 ml four-necked flask equipped with a mechanical stirrer, a thermometer, a Dean-Stark separator, and a reflux condenser, 2.50 g (12.878 mmol) of TMHQA, catalyst (see hylene carbonate and 20 ml of heptane were heated up under argon atmosphere to reflux (oil bath 140 to 145° C.). 3.106 ml (8.585 mmol) of IP were added at a rate of 0.052 ml per minute. Approximately 0.15 ml of water were collected after complete addition of IP. After 20 minutes of stirring heptane was distilled off within approximately 10 minutes. Afterwards the reaction mixture was heated for 60 minutes at 125 to 130° C. The reaction mixture was cooled to 80° C. and 40 ml of heptane were added to the carbonate phase. The reaction mixture was stirred for additional 20 minutes at 60° C. The heptane layer was separated and the ethylene carbonate phase was extracted with heptane (40 ml). The combined heptane phases were evaporated under reduced pressure. A viscous oil comprising (all-rac)-TCPA was obtained. For the yield—based on IP—see table 7.

TABLE 7

Reaction of TMHQA with IP in ethylene carbonate/heptane (v/v = 1/1) in the presence of indium salts.

| Example | Catalyst | Amount of catalyst [mol %] - based on IP | Yield of PTD [%] - based on IP | Yield of TCP [%] - based on IP | Yield of TCPA [%] - based on IP |
|---|---|---|---|---|---|
| 32 | $InCl_3$ | 2 | 14.02 | 0.5 | 84.6 |
| 33 | $In(OTf)_3$ | 0.1 | 4.04 | 11.96 | 57.9 |
| 34* | $In(OTf)_3$ | 0.1 | 9.88 | 16.33 | 62.1 |

*The ethylene carbonate phase of the previous experiment containing catalyst and 4.29 mmol of unreacted TMHQA was reused. One equivalent of TMHQA was added to the ethylene carbonate phase to restore the 1.5 to 1 ratio of TMHQA to IP.

Example 35-41

Preparation of (all-rac)-TCPA from TCP

A 230 ml four-necked flat-bottomed flask with heating/cooling jacket equipped with a thermometer, a glass-tube for the argon purge, a reflux condenser and a mechanical stirrer was filled with certain amounts of the catalyst (see Table 8) and 58.22 g (133 mmol) of (all-rac)-TCP (98.4%). Within 3 minutes 40.64 g (400 mmol, 37.60 ml) of acetic anhydride, $Ac_2O$, were added under stirring. Samples were submitted to qualitative GC-analysis. The results are summarized in Table 8.

TABLE 8

Acetylation of (all-rac)-TCP with $Ac_2O$ (molar ratio 1:3) in the presence of indium salts.

| Example | Catalyst | Amount of catalyst [mol %] - based on TCP | Reaction temperature [° C.] | Reaction time [hour(s)] | Conversion [%] |
|---|---|---|---|---|---|
| 35 | $InCl_3$ | 1.0 | 100 | 3 | >99.99 |
| 36 | $InCl_3$ | 0.1 | 100 | 1 | >99.99 |
| 37 | $InCl_3$ | 0.1 | 25 | 1 | >99.99 |
| 38 | $InCl_3$ | 0.01 | 25 | 9 | >99.99 |
| 39 | $In(OTf)_3$ | 0.1 | 25 | 0.17 | >99.99 |
| 40 | $In(OTf)_3$ | 0.01 | 25 | 0.17 | >99.99 |
| 41 | $In(OAc)_3$ | 1.0 | 50 | 32 | 98.62 |

Examples 42-46

Preparation of (all-rac)-TCPA from TCP with Varying Amounts of Catalyst and $Ac_2O$ Example 39 was repeated, but with varying amounts of the catalyst and $Ac_2O$. The reaction time differed also in the examples 42-46. For a better comparison the results of examples 39 and 40 were also incorporated in the following Table 9, which presents the results of examples 42-46.

TABLE 9

Acetylation of (all-rac)-TCP with Ac$_2$O in the presence of In(OTf)$_3$ as the catalyst.

| Example | Amount of catalyst - based on TCP [mol %] | Molar ratio TCP/Ac$_2$O | Reaction time [hour(s)] | Conversion [%] |
|---|---|---|---|---|
| 39 | 0.1 | 1/3 | 0.17 | >99.99 |
| 40 | 0.01 | 1/3 | 0.17 | >99.99 |
| 42 | 0.001 | 1/3 | 5.66 | 0 |
| 43 | 0.0075 | 1/3 | 3.33 | 99.99 |
| 44 | 0.01 | 1/1.2 | 0.17 | 99.96 |
| 45 | 0.01 | 1/1.1 | 5 | 98.16 |
| 46 | 0.01 | 1/1 | 28 | 90.1 |

Example 47

Preparation of (2R,4'R,8'R)-α-TCPA

A 230 ml four-necked flat-bottomed flask with heating/cooling jacket equipped with a thermometer, a glass-tube for Ar-purge, a reflux condenser and a mechanical stirrer was filled with 2.6 mg of In(OTf)$_3$ (0.01 mol %—based on (2R,4'R,8'R)-α-TCP) and 21.08 g (47.06 mmol) of (2R,4'R,8'R)-α-TCP and a brown oil was obtained. Within 10 minutes 14.56 g (141.2 mmol, 13.47 ml) of Ac$_2$O were added under stirring at 400 rounds per minute. During addition the reaction mixture turned dark brown to finally black. The temperature of the reaction mixture reached 32° C. after 4 minutes of addition, then cooled down to 25° C. for all the remaining time of the reaction. Samples of the reaction mixture were taken and analyzed by qualitative GC analyses. After 4.5 hours the reaction was quenched by the addition of 0.2 g (1.89 mmol) of sodium bicarbonate and the resulting solution was concentrated under reduced pressure to yield the crude product as an orange viscous oil. This oil was purified by bulb-to-bulb distillation (0.009 mbar, 200° C.) using a Kugelrohr apparatus to give (2R,4'R,8'R)-α-TCPA (21.582 g, 97.0% yield—based on (2R,4'R,8'R)-α-TCP). Chiral HPLC analysis showed no trace of its (2S,4'R,8'R) epimer.

Example 48

Preparation of (all-rac)-γ-tocopheryl Acetate from γ-tocopherol (γ-TCP)

A 230 ml four-necked flat-bottomed flask with heating/cooling jacket equipped with a thermometer, a glass-tube for Ar-purge, a reflux condenser and a mechanical stirrer was filled with In(OTf)$_3$ (0.01 mol %—based on γ-TCP; 2.7 mg) and 20.82 g (47.33 mmol) of (all-rac)-γ-tocopherol and a brown solution was obtained. Within 10 minutes 14.615 g (142 mmol, 13.530 ml) of Ac$_2$O were added under stirring at 400 rounds per minute. During addition the reaction mixture turned dark brown to finally black. The temperature of the reaction mixture reached 28° C. after 1 minute of addition, then cooled down to 25° C. for all the remaining time of the reaction. Samples of the reaction mixture were taken and diluted with 1 ml of ethyl acetate before being analyzed by qualitative GC. After 21.66 hours the reaction was quenched by addition of sodium bicarbonate (1.89 mmol, 0.2 g) and the resulting solution was concentrated under reduced pressure to lead to the crude product in form of a dark orange viscous oil. This oil was purified by a bulb-to-bulb distillation using a Kugelrohr apparatus to afford (all-rac)-γ-tocopheryl acetate as a yellow oil (20.761 g, 95.6% yield).

Example 49

Preparation of (all-rac)-α-tocopherol via PTMHQ

In a 50-ml four-necked flask equipped with a mechanical stirrer, a reflux condenser and a thermometer 0.734 g (1.70 mmol) of PTMHQ prepared according to example 5 (see also Table 1), 0.5 mol % of In(OTf)$_3$, and 20 ml of Jeffsol EC-50® were stirred under an argon atmosphere at 135° C. for 1 hour. Afterwards the reaction mixture was cooled down to room temperature and the carbonate phase was extracted with heptane (2×30 ml). The combined heptane phases were concentrated under reduced pressure to yield 0.74 g of (all-rac)-TCP as a yellow oil. The overall yield—based on IP—is 92.2%.

Examples 50-51

Preparation of (all-rac)-TCP at Atmospheric Pressure

In a 250 ml Büchi reactor or an autoclave equipped with a stirrer, a thermometer, a pressure indicator, a Dean-Stark separator, and a reflux condenser 30.447 g (200 mmol) of TMHQ (99.97%), certain amounts of InCl$_3$ (see Table 10; amounts based on IP) and 100 ml of toluene were heated at 114° C. under a continuous nitrogen flow and under an absolute pressure of 1.0 bar. 74.035 ml (200 mmol) of IP (94.6%,) were added at a feed rate of 1.234 ml per minute. Approximately 3.6 ml of water were collected until the end of the reaction. After completion of the addition the reaction mixture was stirred for 1 hour at 114° C. and cooled down to room temperature. Then the reaction mixture was concentrated under reduced pressure (45° C. at 95 to 15 mbar). (all-rac)-TCP was obtained as a viscous oil. For the results see Table 10.

Example 52**

Example 51 was repeated, but instead of toluene heptane was used as the solvent.

Examples 53-54

Preparation of (all-rac)-TCP under Pressure

Examples 50 and 51 were repeated, but the reaction was carried out at 137° C. under an absolute pressure of 2 bar. After 1 hour at 137° C. the reaction mixture was cooled down to room temperature and once at room temperature the pressure was released.

Example 55**

Preparation of (all-rac)-TCP Under Pressure

In a 250 ml Büchi reactor or an autoclave equipped with a stirrer, a thermometer, a pressure indicator, a Dean-Stark separator, and a reflux condenser, 30.447 g (200 mmol) of TMHQ (99.97%), 5 ml of InCl$_3$ (0.2 M aqueous solution, 0.5 mol %, 1 mmol) and 100 ml of heptane were heated at 147° C. under a continuous nitrogen flow and under an absolute pressure of 3.4 bar. 75.304 ml (203 mmol) of IP (94.6%) were added at a feed rate of 0.605 ml per minute. Approximately 3.6 ml of water were collected until the end of the reaction. After completion of the addition of IP the reaction mixture was stirred for 1 hour at 147° C. and cooled down to room temperature. Then the pressure was released. The reaction mixture was concentrated under reduced pressure (45° C. at 110 to 15 mbar). (all-rac)-TCP was obtained as a viscous oil (91.51 g). The yield was 92.0%—based on IP.

TABLE 10

Comparison between experiments at atmospheric pressure and under pressure in toluene with $InCl_3$ as the catalyst. The conversion of IP was 100% in all cases.

| Example | Catalyst | Amount of catalyst [mol %] | Solvent | Pressure [bar] | Yield of TCP [%] = Selectivity for TCP [%] |
|---|---|---|---|---|---|
| 50 | $InCl_3$ | 2.0 | toluene | 1.0 | 90.1 |
| 51 | $InCl_3$ | 0.5 | toluene | 1.0 | 59.8 |
| 52** | $InCl_3$ | 0.5 | toluene | 1.0 | 18.5 |
| 53 | $InCl_3$ | 2.0 | toluene | 2.0 | 95.7 |
| 54 | $InCl_3$ | 0.5 | toluene | 2.0 | 81.2 |
| 55** | $InCl_3$ | 0.5 | heptane | 3.4 | 92.0 |

Examples 56 and 58(***)

Preparation of (all-rac)-TCP with an Excess of IP 200 mmol of TMHQ and 203 mmol of IP (corresponding a molar excess of 1.38%) were reacted in 100 ml of toluene at 137° C. or in 100 ml of heptane at 147° C. The IP was added during 120 minutes. Afterwards the mixture was reacted for further 60 minutes. All yields and selectivities (given in Table 11) are based on IP.

Examples 57, 59 and 60

Preparation of (all-rac)-TCP with Different Indium Salts as the Catalyst 200 mmol of TMHQ and 200 mmol of IP were reacted in 100 ml of toluene at 137° C. or in 100 ml of heptane at 147° C. The IP was added during 60 minutes. Afterwards the mixture was reacted for further 60 minutes. All yields and selectivities (given in Table 11) are based on IP.

TABLE 11

Influence of the counterion of the indium salt. The amount of catalyst was 2.0 mol %, based on IP, in all cases. The conversion of IP was 100% in all cases.

| Example | Catalyst | Solvent | Pressure [bar] | Yield of TCP [%] = Selectivity for TCP [%] |
|---|---|---|---|---|
| 53 | $InCl_3$ | Toluene | 2.0 | 95.7 |
| 56*** | $InCl_3$ | Toluene | 2.0 | 95.5 |
| 57 | $InCl_3$ | Heptane | 3.4 | 89.5 |
| 58*** | $InCl_3$ | Heptane | 3.4 | 93.9 |
| 59 | $In(OTf)_3$ | Toluene | 2.0 | 72.3 |
| 60 | $In(OTf)_3$ (2) | Heptane | 3.4 | 65.6 |

With $InCl_3$ excellent yields were obtained in both solvents, heptane and toluene. The selectivity for the formation of the desired 6-membered ring product (all-rac)-TCP with this catalyst was very high compared to results with $In(OTf)_3$ as a difference of 28 to 30% for the selectivity was observed.

It was also found that a small excess of IP (+1.38%) led to a much better yield (see Table 11, example 58). In fact, (all-rac)-TCP could be isolated in 93.9% yield after work-up. It has to be emphasized that at atmospheric pressure a TMHQ/IP ratio of 1.5/1 was used whereas, under pressure, an equimolar ratio was sufficient to produce the desired chroman ring compound (all-rac)-TCP in excellent yield.

It is noteworthy that the proportion of TMHQ used for these reactions under pressure was twenty-fold higher than at atmospheric pressure (4 mol/l instead of 0.2 mol/l) and it did not affect the yield of the reaction.

Example 61

Preparation of (all-rac)-TCP 200 mmol of TMHQ and 203 mmol of IP were reacted in 100 ml of toluene at 137° C. The IP was added during 120 minutes. The reaction mixture was then further reacted for another 60 minutes. The yield—based on IP—is given in Table 12.

Example 62

Preparation of (all-rac)-TCP 200 mmol of TMHQ and 203 mmol of IP were reacted in 100 ml of toluene at 137° C. The IP was added during 120 minutes. The reaction mixture was then reacted for further 566 minutes. The yield—based on IP—is given in Table 12.

Example 63

Preparation of (all-rac)-TCP 200 mmol of TMHQ and 203 mmol of IP were reacted in 100 ml of heptane at 147° C. The IP was added during 120 minutes. The reaction mixture was then further reacted for another 120 minutes. The yield—based on IP—is given in Table 12.

TABLE 12

Influence of the amount of $InCl_3$. The conversion of IP was 100% in all cases.

| Example | Amount of $InCl_3$ [mol %] | Solvent | Pressure [bar] | Yield of TCP [%] = Selectivity for TCP [%] |
|---|---|---|---|---|
| 52 | 0.5 | Heptane | 1.0 | 18.5 |
| 55 | 0.5 | Heptane | 3.4 | 92.0 |
| 56 | 2 | Toluene | 2.0 | 95.5 |
| 58 | 2 | Heptane | 3.4 | 93.9 |
| 61 | 0.5 | Toluene | 2.0 | 90.2 |
| 62 | 0.25 | Toluene | 2.0 | 85.1 |
| 63 | 0.25 | Heptane | 3.4 | 81.5 |

When the amount of $InCl_3$ was reduced to 0.25 mol % (all-rac)-TCP was obtained in good yield (see Table 12, examples 62 and 63). However a longer reaction time (e.g. up to 566 minutes in toluene) was needed to obtain nearly total ring closure.

It appeared that a good balance between selectivity for (all-rac)-TCP, yield and catalyst amount was the use of 2 mol % $InCl_3$, especially in heptane. In toluene and in heptane, the desired chroman product (all-rac)-TCP could be isolated in up to 95.5% yield.

Example 64

Preparation of (all-rac)-TCP 200 mmol of TMHQ and 203 mmol of IP were reacted in 100 ml of cyclohexane at 135° C. and under an absolute pressure of 4.0 bar in the presence of 0.5 mol % of InCl$_3$—based on IP. The IP was added during 120 minutes. Afterwards the mixture was reacted for further 380 minutes. The yield of (all-rac)-TCP given in Table 13 is based on IP.

Example 65

Preparation of (all-rac)-TCP 200 mmol of TMHQ and 203 mmol of IP were reacted in 100 ml of hexane in the presence of 0.5 mol % of InCl$_3$—based on IP. The IP was added during 120 minutes at 125° C. and under an absolute pressure of 4.0 bar. Afterwards the mixture was reacted for further 180 minutes at 125° C. and under an absolute pressure of 4.0 bar and further 206 minutes at 135° C. and under an absolute pressure of 5.1 bar. The yield of (all-rac)-TCP given in Table 13 is based on IP.

TABLE 13

Influence of the solvent. The conversion of IP was 100% in all cases.

| Example | Solvent | Temperature of the reaction mixture [° C.] | Pressure [bar] | Yield of TCP [%] = Selectivity for TCP [%] |
|---|---|---|---|---|
| 55 | Heptane | 147 | 3.4 | 92.0 |
| 61 | Toluene | 137 | 2.0 | 90.2 |
| 64 | Cyclohexane | 135 | 4.0 | 86.6 |
| 65 | Hexane | 125/135 | 4.0/5.1 | 75.1 |

One of the advantages of heptane compared to toluene was the absence of by-products such as phytyl-toluene compounds due to the solvent.

Examples 55-a to 55-e

Reproducibility

All reactions were carried out in 100 ml of heptane with 200 mmol of TMHQ, 203 mmol of IP, 0.5 mol % of InCl$_3$ under an absolute pressure of 3.4 bar and at 147° C. IP as added within 120 minutes. The reaction time was 60 minutes. All yields are based on IP. The results are summarized in Table 14.

TABLE 14

Test of reproducibility, total conversion of IP:

| Example | Yield of TCP [%] = Selectivity for TCP [%] |
|---|---|
| 55-a | 92.0 |
| 55-b | 91.8 |
| 55-c | 90.6 |
| 55-d | 92.3 |
| 55-e | 91.2 |

An excellent reproducibility was found as only a 1.04% maximum variation of the yield was observed with an average yield of 91.6% over five experiments.

Examples 53, 55-d and 59

Amount of By-Products

For these three experiments the precise analytical data concerning the side products are given in Table 15.

TABLE 15

Detailed results and comparison of selectivity

| | Example | | |
|---|---|---|---|
| | 53 | 55-d | 59 |
| Amount of TMHQ to IP [mmol] | 200/200 | 200/203 | 200/200 |
| Catalyst and amount in mol % | 2.0 InCl$_3$ | 0.5 InCl$_3$ | 2.0 In(OTf)$_3$ |
| Solvent | toluene | heptane | toluene |
| Temperature of the reaction mixture [° C.] | 137 | 147 | 137 |
| Pressure [bar] | 2.0 | 3.4 | 2.0 |
| Time for the addition of IP [minutes] | 60 | 126 | 60 |
| Crude product[g] | 94.42 | 92.96 | 101.4 |
| Content of DHTC according to GC [%] | 0.00 | 0.15 | 0.00 |
| Content of BZF according to GC [%] | 0.33 | 0.31 | 7.43 |
| Content of TCP according to GC [%] | 87.28 | 86.84 | 61.45 |
| Yield of TCP [%] | 95.7 | 93.7 | 72.3 |

As already stated, InCl$_3$ shows a higher selectivity for the formation of TCP than In(OTf)$_3$.

The invention claimed is:

1. An alkenylation process comprising carrying out an alkenylation, in the presence of an indium (III) salt catalyst, of an aromatic compound containing at least one hydroxy group with a compound of formula III and/or a compound of formula IV in an organic solvent

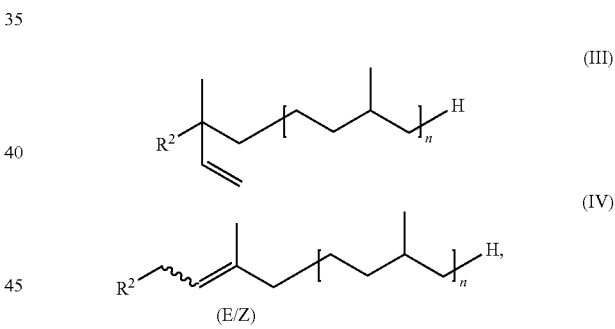

wherein the aromatic compound containing at least one hydroxy group has at least one unsubstituted position, as well as 0-to-4 linear $C_{1-6}$-alkyl groups and a total of 1-to-3 hydroxy groups, $R^2$ is hydroxy, acetyloxy, benzoyloxy or halogen, n is an integer of from 0-to-3, and the organic solvent is an aprotic non-polar organic solvent, an aprotic polar solvent or a two-phase solvent system comprising one or more aprotic non-polar organic solvents and one or more aprotic polar solvents, where the aprotic non-polar organic solvent(s) is/are selected from the group consisting of aliphatic hydrocarbons, aromatic hydrocarbons, halogenated aliphatic hydrocarbons, halogenated aromatic hydrocarbons, and mixtures of two or more thereof, and the aprotic polar solvent(s) is/are selected from the group consisting of aliphatic carbonates, cyclic carbonates, aliphatic esters, cyclic esters, aliphatic ketones, cyclic ketones and mixtures of two or more thereof.

2. The process as claimed in claim 1 wherein the aromatic compound having at least one hydroxy group is a compound of the formula II

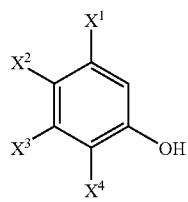

(II)

wherein $X^1$, $X^2$, $X^3$ and $X^4$ are independently selected from the group consisting of hydrogen, hydroxy and linear $C_{1-6}$-alkyl.

3. The process as claimed in claim 1 wherein the aromatic compound having at least one hydroxy group is a compound of the formula IIa

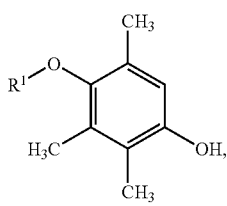

(IIa)

wherein $R^1$ is selected from the group consisting of hydrogen, acetyl, propionyl, pivaloyl, $HO_2C$—$CH_2$—$CH_2$—CO, nicotinoyl and palmityl.

4. A process for the manufacture of compounds of formula VII

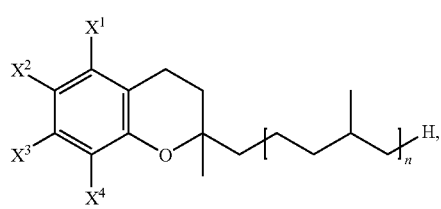

(VII)

comprising a) optionally alkenylating a phenol of formula II

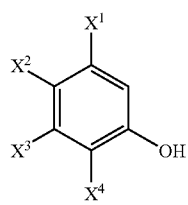

(II)

with a compound of formula III and/or a compound of formula IV in an organic solvent

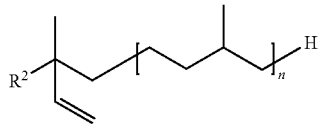

(III)

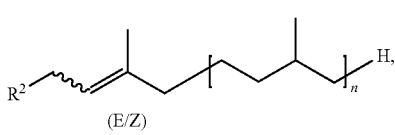

(IV)

(E/Z)

and b) submitting a compound of formula I

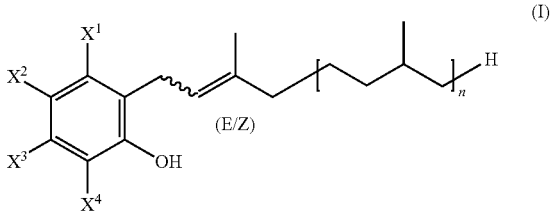

(I)

(E/Z)

and optionally one or more double-bond isomers thereof, all obtainable by step a, to ring closure in an organic solvent to form the compound of formula VII, wherein $X^1$, $X^3$ and $X^4$ are independently selected from the group consisting of hydrogen, hydroxy and linear $C_1$-$C_6$-alkyl; $X^2$ is hydrogen, hydroxy, linear $C_1$-$C_6$-alkyl, or, when $X^1$, $X^3$ and $X^4$ are each $CH_3$, is $OR^1$, where $R^1$ is selected from the group consisting of hydrogen, acetyl, propionyl, pivaloyl, $HO_2C$—$CH_2$—$CH_2CO$, nicotinoyl and palmityl; $R^2$ is hydroxy, acetyloxy, benzoyloxy or halogen; n is an integer of from 0-to-3, and the organic solvent in steps a) and b) is an aprotic non-polar organic solvent, an aprotic polar solvent, or a two-phase solvent system comprising one or more aprotic non-polar organic solvents and one or more aprotic polar solvents, where the aprotic non-polar organic solvent(s) is/are selected from the group consisting of aliphatic hydrocarbons, aromatic hydrocarbons, halogenated aliphatic hydrocarbons, halogenated aromatic hydrocarbons and mixtures of two or more thereof, and the aprotic polar solvent(s) is/are selected from the group consisting of aliphatic carbonates, cyclic carbonates, aliphatic esters, cyclic esters, aliphatic ketones, cyclic ketones, and mixtures of two or more thereof; and c) carrying out at least one of steps a and b in the presence of an indium (III) salt catalyst.

5. A process for the manufacture of esters of compounds of formula VII

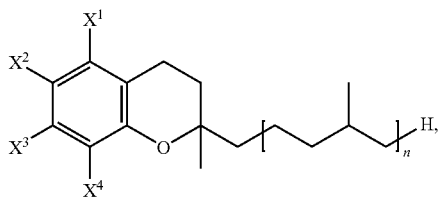

(VII)

wherein $X^1$, $X^3$ and $X^4$ are independently selected from the group consisting of hydrogen, and methyl; $X^2$ is hydroxy, and n is 3, the process comprising reacting a compound of formula VII with an acylating agent in the presence of an indium (III) salt catalyst.

6. The process as claimed in claim 5, wherein the compound of formula VII is α-tocopherol which is reacted with an acylating agent selected from the group consisting of acetic acid, propionic acid, pivalic acid, succinic acid, nicotinic acid, palmitic acid, benzoic acid, their anhydrides and halides, to obtain the corresponding α-tocopheryl esters.

7. The process as claimed in claim 5, wherein the reaction is carried out at an absolute pressure from at least 0.02 bar.

8. The process as claimed in claim 1, wherein the indium (III) salt is indium trichloride or indium tris(trifluoromethanesulfonate).

9. The process according to claim 1, wherein at least one step is carried out at an absolute pressure of at least 0.96 bar.

10. The process according to claim 4, wherein all steps are carried out at an absolute pressure of at least 0.96 bar.

11. The process according to claim 1, wherein the catalyst is used in an amount of from 0.1-to-2 mol % based on the compound represented by formula III or formula IV.

12. The process according to claim 1, wherein the reaction is carried out in a non-polar organic solvent selected from the group consisting of cyclohexane, hexane, heptane, octane, 1,1,1-trichloroethane, 1,2-dichloroethane, methylene chloride, methylene bromide, benzene, toluene, o-xylene, m-xylene, p-xylene, chlorobenzene, 1,2-dichlorobenzene, 1,3-dichlorobenzene and 1,4-dichlorobenzene.

13. The process according to claim 1, wherein the solvent is a two-phase solvent system, where one phase of the two-phase solvent system is ethylene carbonate or propylene carbonate or a mixture thereof, and the other phase is hexane, heptane, or octane.

14. The process according to claim 5, wherein the catalyst is used in an amount of from 0.0075-to-2 mol % based on the compound of formula VII.

15. A process for the manufacture of alkanoates of α-tocopherol, β-tocopherol, γ-tocopherol and δ-tocopherol, wherein α-tocopherol, β-tocopherol, γ-tocopherol and δ-tocopherol, respectively, obtained by a process according to claim 4 is reacted with an acylating agent.

16. A process for the manufacture of formulations of α-tocopherol, β-tocopherol, γ-tocopherol, δ-tocopherol or their alkanoates, whereby α-tocopherol, β-tocopherol, γ-tocopherol, δ-tocopherol or their alkanoates, respectively, is obtained by a process according to claim 5.

17. A process for the manufacture of esters of compounds selected from the group consisting of aromatic compounds having at least one hydroxy group, the process comprising reacting an aromatic compound having at least one hydroxy group with an acylating agent in the presence of an indium (III) salt catalyst, wherein the catalyst is present in an amount of from 0.006-to-0.01 mol % based on the aromatic compound.

18. The process as claimed in claim 5, wherein the compound of the formula VII is α-tocopherol, which is reacted with an acylating agent selected from the group consisting of acetic acid, propionic acid, pivalic acid, succinic acid, nicotinic acid, palmitic acid, benzoic acid, their anhydrides and halides, to obtain the corresponding α-tocopheryl esters.

19. The process as claimed in claim 17, wherein the reaction is carried out at an absolute pressure from at least 0.02 bar.

20. The process according to claim 4, wherein each of $X^1$, $X^3$ and $X^4$ is $CH_3$, and $X^2$ is $OR^1$, where $R^1$ is selected from the group consisting of hydrogen, acetyl, propionyl, pivaloyl, $HO_2C$—$CH_2$—$CH_2$—$CO$, nicotinoyl and palmityl, $R^2$ is hydroxy, acetyloxy, benzoyloxy or halogen, and n is 3.

21. The process according to claim 20, wherein $R^2$ is hydroxy.

22. The alkenylation process according to claim 3, wherein n is 3.

23. The alkenylation process according to claim 22, wherein $R^2$ is hydroxy.

24. The process according to claim 5, wherein n is 3 and the acylating agent is selected from the group consisting of acetic acid, propionic acid, pivalic acid, succinic acid, nicotinic acid, palmitic acid, benzoic acid, their anhydrides and halides.

25. The process according to claim 20, wherein $R^1$ is hydrogen or acetyl.

26. The alkenylation process according to claim 22, wherein $R^1$ is hydrogen or acetyl.

27. The process according to claim 25, wherein $R^1$ is acetyl.

28. The process according to claim 24, wherein the reaction is carried out at an absolute pressure from at least 0.02 bar.

29. The process according to claim 20, wherein the catalyst is used in an amount of from 0.0075-to-2 mol % based on the compound of formula VII, wherein $X^2$ is $OR^1$.

30. A process for the manufacture of esters of compounds of the formula:

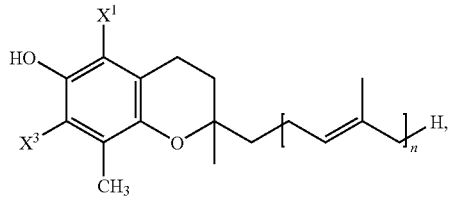

wherein $X^1$ and $X^3$ are independently selected from the group consisting of hydrogen and methyl, and n is 3, the process comprising reacting said compounds with an acylating agent in the presence of an indium (III) salt catalyst.

* * * * *